(12) United States Patent
O'Neil et al.

(10) Patent No.: US 8,889,724 B2
(45) Date of Patent: *Nov. 18, 2014

(54) TETRAZOLE COMPOUNDS FOR REDUCING URIC ACID

(71) Applicant: Wellstat Therapeutics Corporation, Gaithersburg, MD (US)

(72) Inventors: James Dennen O'Neil, Frederick, MD (US); Shalini Sharma, Gaithersburg, MD (US); Ramachandran Arudchandran, Germantown, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/783,680

(22) Filed: Mar. 4, 2013

(65) Prior Publication Data

US 2013/0336949 A1    Dec. 19, 2013

Related U.S. Application Data

(63) Continuation of application No. 12/989,724, filed as application No. PCT/US2009/042298 on Apr. 30, 2009, now Pat. No. 8,410,154.

(60) Provisional application No. 61/049,167, filed on Apr. 30, 2008, provisional application No. 61/093,743, filed on Sep. 3, 2008.

(51) Int. Cl.
    *A61K 31/41*     (2006.01)
    *C07D 257/04*    (2006.01)
    *A61K 45/06*     (2006.01)

(52) U.S. Cl.
    CPC .............. *C07D 257/04* (2013.01); *A61K 31/41* (2013.01); *A61K 45/06* (2013.01)
    USPC .......................................... 514/381; 548/252

(58) Field of Classification Search
    None
    See application file for complete search history.

(56) References Cited

U.S. PATENT DOCUMENTS

| | | | |
|---|---|---|---|
| 4,021,556 | A | 5/1977 | Springer et al. |
| 4,024,253 | A | 5/1977 | Umezawa et al. |
| 4,182,764 | A | 1/1980 | Cragoe, Jr. et al. |
| 4,845,231 | A | 7/1989 | Kees |
| 4,874,777 | A | 10/1989 | Carr et al. |
| 5,100,910 | A | 3/1992 | Milcent et al. |
| 5,591,862 | A | 1/1997 | Sohda et al. |
| 6,376,512 | B1 | 4/2002 | Jayyosi et al. |
| 7,041,659 | B2 | 5/2006 | Sharma |
| 7,851,494 | B2 | 12/2010 | Sharma et al. |
| 8,410,154 | B2 | 4/2013 | O'Neil et al. |
| 2003/0040535 | A1 | 2/2003 | Aspnes et al. |
| 2004/0019208 | A1 | 1/2004 | Nivorozhkin et al. |
| 2005/0256333 | A1 | 11/2005 | Sharma et al. |
| 2006/0135519 | A2* | 6/2006 | Nivorozhkin et al. ..... 514/235.5 |
| 2007/0010670 | A1 | 1/2007 | Hirata et al. |
| 2008/0015209 | A1 | 1/2008 | Sharma et al. |

FOREIGN PATENT DOCUMENTS

| | | |
|---|---|---|
| EP | 0480659 A2 | 4/1992 |
| EP | 11227882 A1 | 8/2001 |
| EP | 0888278 B1 | 7/2003 |
| RU | 2144533 C1 | 1/2000 |
| WO | 03/082205 A2 | 10/2003 |
| WO | 2004/009563 A1 | 1/2004 |
| WO | 2004/080480 A1 | 9/2004 |
| WO | 2009/151695 A1 | 12/2009 |

OTHER PUBLICATIONS

Armstrong, KA, et al., "Does Uric Acid Have a Pathogenetic Role in Graft Dysfunction and Hypertension in Renal Transplant Patients?," Transplantation, 80(11):1565-1571 (2005).

Avaram, V., and E. Krishnan, "Hyperuricemia—Where Nephrology Meets Rheumatology," Rheumatology (Oxford), 47(7): 960-964 (2008).

Bainbridge. SA and Roberts, JM, "Uric Acid as a Pathogenic Factor in Preeclampsia," Placenta 29, Supplement A, Trophoblast Research, vol. 22: S67-S72 (2008).

Bos et al., "Uric Acid is a Risk Factor for Myocardial Infarction and Stroke: the Rotterdam Study," Stroke. 37(6): 1503-1507 (Jun. 2006).

Cengel A., et al., "Serum uric Acid Levels as a Predictor of In-hospital Death in Patients Hospitalized for Decompensated Heart Failure," Acta Cardiol, 60(5): 489-492 (Oct. 2005).

Chien, K-L, et al., "Plasma Uric Acid and the Risk of Type 2 Diabetes in a Chinese Community," Clin. Chem. 54(2): 310-316 (2008).

Cirillo, et al., "Uric Acid. The Metabolic Syndrome, and Renal Disease," J Am Soc Nephrol., 17:S165-8 (2006).

Coutinho, et al "Associations of Serum Uric Acid with Markers of Inflammation, Metabolic Syndrome. and Subclinical Coronary Atherosclerosis," Amer. J. Hypertens, 20:83-89 (2007).

Feig, Di, and Johnson, RJ, "The Role of Uric Acid in Pediatric Hypertension," J Ren Nutrition, 17(1):79-83 (2007).

(Continued)

*Primary Examiner* — Michael Barker
(74) *Attorney, Agent, or Firm* — Lewis J. Kreisler

(57) ABSTRACT

Uric acid in mammalian subjects is reduced and excretion of uric acid is increased by administering a compound of Formula I. The uric acid-lowering effects of the compounds of this invention are used to treat or prevent a variety of conditions including gout, hyperuricemia, elevated levels of uric acid that do not meet the levels customarily justifying a diagnosis of hyperuricemia, renal dysfunction, kidney stones, cardiovascular disease, risk for developing cardiovascular disease, tumor-lysis syndrome, cognitive impairment, early-onset essential hypertension, and *Plasmodium falciparum*-induced inflammation.

(I)

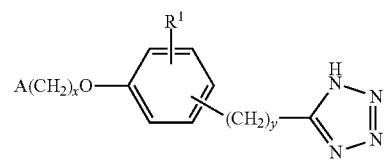

16 Claims, 9 Drawing Sheets

(56) References Cited

OTHER PUBLICATIONS

Feig, Di, et al., "Effect of Allopurinol on Blood Pressure of Adolescents With Newly Diagnosed Essential Hypertension" JAMA, 300(8): 924-932 ( 2008).
Halevy et al., "Allopurinol is the Most Common Cause of Stevens-Johnson Syndrome and Toxic Epidermal Necrolysis in Europe and Israel," J Am Acad Dermatol., 58(1):25-32 (2008).
Inokuchi, T., et al., "Plasma IL-18 and Other Inflammatory Cytokines in Patients With Gouty Arthritis and Monosodium Urate Monohydrate Crystal-Induced Secretion of IL-18," Cytokine., 33(1): 21-27 (2006).
Ioachimescu, AG, et al. "Serum Uric Acid, Mortality and Glucose Control in Patients With Type 2 Diabetes Mellitus: a Precis Database Study," Diabet. Med., 24(12):1369-1374 (2007).
Ishizaka, N., et al., "Association Between Serum Uric Acid, Metabolic Syndrome, and Carotid Atherosclerosis in Japanese Individuals," Arterioscler Thromb Vasc Biol., 25: 1038-44 (2005).
Jee, Sa, et al. "Serum Uric Acid and Risk of Death From Cancer. Cardiovascular Disease or All Causes in Men," Eur. J. Cardiovascular Prev. Rehab., 11(3):185-191 (2004).
Kanellis, J., and Kang, D-H., "Uric Acid as a Mediator of Endothelial Dysfunction, Inflammation, and Vascular Disease," Semin Nephrol., 25(1); 39-42 (2005).
Kang, D-H., et al., "Uric Acid Causes Vascular Smooth Muscle Cell Proliferation by Entering Cells Via a Functional Urate Transporter," Am J Nephrol. 2005 25(5):425-33 (2005).
Khosla, Um, et al., "Hyperuricemia Induces Endothelial Dysfunction," Kidney Int. 67(5):1739-42 (2005).
Krishnan, E., et al. "Gout in Ambulatory Care Settings in the United States," Journal of Rheumatology, 35(3): 498-501 (2008).
Lehto, S., et al., "Serum Uric Acid is a Strong Predictor of Stroke in Patients With Non-Insulin Dependent Diabetes Mellitus," Stroke, 29: 635-639 (1998).
Leyva, F., et al., "Uric Acid in Chronic Heart Failure: A Marker of Chronic Inflammation", Eur. Heart J., 19(12): 1814-1822 (1998).
Mikuls, TR, et al. "Gout Epidemiology; Results from the UK General Practice Research Database, 1990-1999." Annals of the Rheumatic Diseases, 64:267-272 (2005).
Orengo, JM, et al., "Uric Acid is a Mediator of the Plasmodium falciparum-Induced Inflammatory Response," PLoS One 4(4): e5194. doi:10.13711journal.pone.0005194, (2009).
Pascual-Figal, DA, et al., "Hyperuricaemia and Long-Term Outcome After Hospital Discharge in Acute Heart Failure Patients," Eur J Heart Fail., 9:518-524 (2007).
Perlstein, TS, et al., "Uric Acid and the State of the Intrarenal Renin-Angiotensin System in Humans," Kidney International. 66:1465-1470 (2004).
Perry, IJ, et al., "Prospective Study of Risk Factors for Development of Non-Insulin Dependent Diabetes in Middle Aged British Men," BMJ, 310 (6979): 560-564 (1995).
Price, KL, et al., "Human Vascular Smooth Muscle Cells Express a Urate Transporter," J Am Soc Nephrol. 17(7): 1791-1795 (2006).

Reidel, AA, et al. "Compliance with Allopurinol Therapy Among Managed Care Enrollees with Gout: A Retrospective Analysis of Administrative Claims," Journal of Rheumatology, 31:1575-1581 (2004).
Ruggiero, C., et al., "Uric Acid and Inflammatory Markers," European Heat Journal, 27:1174-1181 (2006).
Saito. H. et al., "Tissue Hypoxia in Sleep Apnea Syndrome Assessed by Uric Acid and Adenosine," Chest, 122: 1686-1694 (2002).
Sautin, YY, et al., "Adverse Effects of the Classic Antioxidant Uric Acid in Adipocytes: NADPH Oxidase-Mediated Oxidative/Nitrosative Stress," Am. J. Physiol. Cell Physiol., 293: C584-C596 (2007).
Schretlen. DJ, et al., "Serum Uric Acid and Cognitive Function in Community-Dwelling Older Adults", Neuropsychology, 21(1): 136-140 (Jan. 2007).
Shankar, A, et al., "Association Between Serum Uric Acid Level and Peripheral Artery Disease," Atherosclerosis, doi 10: 1016, (Epub 2007), vol. 196(2): 74-755 (2008).
Stamp, L., et al. "Gout in Solid Organ Transplantation: A Challenging Clinical Problem", Drugs, 65(18):2593-2611 (2005).
Strasak. AM et al., "Serum Uric Acid and Risk of Cancer Mortality in a Large Prospective Male Cohort," Cancer Causes Control, 18(9):1021-1029,(2007).
Strasak, AM et al., "The Role of Serum Uric Acid as an Antioxidant Protecting Against Cancer: Prospective Study in More Than 28,000 Older Austrian Women," Annals Oncol., 18(11):1893-1897 (2007).
Strasak. AM, et al., "Serum Uric Acid and Risk of Cardiovascular Mortality; A Prospective, Long-Term Study of 83,683 Austrian Men," Clin Chem., 54(2): 273-284 (2008).
Sundström, J., et al., "Relations of Serum Uric Acid to Longitudinal Blood Pressure Tracking and Hypertension Incidence," Hypertension, 45(1):28-33 (2005).
Syamala, S. et al. "Association Between Serum Uric Acid and Prehypertension Among US Adults," J. Hypertens., 25(8):1583-1589 (2007).
Tseng, CH, "Independent Association of Uric Acid Levels With Peripheral Artery Disease in Taiwanese Patients With Type 2 Diabetes." Diabet. Med., 21(7):724-729 (2004).
Verhulst, SL, et al., "Sleep-Disordered Breathing and Uric Acid in Overweight and Obese Children and Adolescents," Chest, 132:76-80 (2007).
Wallace, KL, et al., "Increasing Prevalence of Gout and Hyperuricemia over 10 Years Among Older Adults in a Managed Care Population," Journal of Rheumatology, 31:1582-1587 (2004).
Watanabe, S., et al. "Cerebral Oxidative Stress and Mitochondrial Dysfunction in Oxonate-Induced Hyperuricemie Mice", J. Health Science, 52(6): 730-737 (2006).
Yamamoto, Y., et al "Allopurinol Reduces Neointimal Hyperplasia in the Carotid Artery Ligation Model in Spontaneously Hypertensive Rats," Hypetens. Res, 29(11): 915-921 (2006).
Zoccali, C., et al., "Uric Acid and Endothelial Dysfunction in Essential Hypertension," J Am Soc Nephrol., 17(5): 1466-71 (2006).
Decision of Grant in connection with Russian Patent Application No. 2010148762. (2012).
Gustafsson, et al., "Review: The pathophysiology of hyperuricaemia and its possible relationship to cardiovascular disease, morbidity and mortality", BMC Nephrology (2013) 14:164.
Office action dated Apr. 17, 2014, in U.S. Appl. No. 13/890,789.

* cited by examiner

TETRAZOLE COMPOUNDS FOR REDUCING URIC ACID

BACKGROUND OF THE INVENTION

Diseases caused by elevated levels of uric acid fall into two major categories: disorders caused by precipitation of uric acid crystals and diseases related to pathological effects of soluble uric acid. Gouty arthritis is the classic example of the former. Deposition of urate crystals in the kidney is also a common cause of renal dysfunction. Elevated levels of soluble uric acid are associated with a variety of disorders, including cardiovascular and renal diseases.

Gout is most commonly manifested as inflammation of one or more of the joints in the body resulting in mild to severe pain. These events may be episodic and/or chronic. Over time gout can result in the destruction of cartilage and bone, development of uric acid crystal deposits, kidney pain and dysfunction as well as kidney stones. Gout can affect other organs as well.

Gout is caused by hyperuricemia and the consequent formation and deposition of uric acid crystals in tissues, joints, kidneys and other organs. The uric acid comes from normal cell metabolism and from some types of foods and beverages. The excessive levels of uric acid are the result of too much uric acid production, impaired clearance by the kidneys (or a combination of excess production and impaired clearance), and also by some forms of medications taken for other health conditions. (Examples include diuretics, pyrazinamide, cyclosporine, low-dose aspirin, nicotinic acid and levodopa.). Many types of health conditions can also contribute to hyperuricemia and gout, including alcoholism, leukemia, lymphoma, lung cancer, tumor-lysis syndrome, smoking, psoriasis, obesity, kidney dysfunction, congestive heart failure, starvation, anemia, high blood pressure, diabetes, immobility, Lesch-Nyhan Syndrome, Down syndrome, and thyroid and parathyroid dysfunctions.

Gout is generally divided into four categories based upon progressively more severe symptoms:
1) Asymptomatic. Elevated uric acid levels in the blood, but no overt symptoms.
2) Acute gouty arthritis: Sudden onset of symptoms, often in a single joint (commonly a big toe), and then involving other joints. Symptoms include pain, swelling, redness and fever.
3) Intercritical gout: Asymptomatic phases between gout attacks.
4) Chronic tophaceous gout: A chronic condition that may include frequent attacks, constant mild pain and inflammation of joints, destruction of cartilage and bone, development of uric acid crystal deposits, kidney dysfunction and kidney stones.

Medications currently used to treat the acute symptoms of gout include nonsteroidal anti-inflammatory drugs, colchicine and corticosteroids. All of these medications can produce mild to severe side effects. Other treatments for these acute symptoms are being studied, including antibodies and antagonists to inflammatory cytokines such as Interleukin 1.

Other types of medication are used in order to try to reduce the incidence or severity of future attacks by reducing levels of uric acid. The three principal classes of medication are xanthine oxidase inhibitors (for example, allopurinol), which reduce production of uric acid from xanthine; uricosuric agents (for example, sulfinpyrazone, probenecid, benzbromarone and losartan), which are intended to improve excretion of uric acid by inhibiting reuptake of secreted uric acid in the renal tubules via inhibition of uric acid transporter 1 (URAT1) (See also US Patent Application Publication No. 2007/0010670, published Jan. 11, 2007 (Japan Tobacco Inc.)) or other elements of uric acid reuptake; and uricases, for example a pegylated-uricase such as PURICASE (Savient's pegylated recombinant mammalian uricase). These medications also often result in significant and undesirable side effects. For example, allopurinol has been reported to cause at least 100 cases of Stevens-Johnson/Toxic Epidermal Necrolysis and approximately 30 deaths each year in Europe (Halevy et al., Allopurinol is the most common cause of Stevens-Johnson syndrome and toxic epidermal necrolysis in Europe and Israel. J Am Acad Dermatol. 58(1):25-32, 2008). Probenicid and benzbromarone have been taken off the market in a number of countries due to undesirable side effects, such as liver failure in the case of benzbromarone. Patient compliance in taking these drugs is reportedly very poor (A. A. Reidel et al. "Compliance with Allopurinol Therapy among Managed Care Enrollees with Gout: A Retrospective Analysis of Administrative Claims." Journal of Rheumatology 2004; 31:1575-1581), presumably because of the side effects and/or lack of benefit.

More than 5 million people in the U.S. have gout (National Health and Nutrition Examination Survey 111, 1988-1994). The prevalence of hyperuricemia and gout in the U.S. in 1999 was reported to be 41 per 1,000 and 14 per 1,000 in the U.K. (T. R. Mikuls et al., "Gout Epidemiology: Results for the UK General Practice Research Database, 1990-1999." Annals of the Rheumatic Diseases 2005; 64:267-272). Subsequent reports indicate that the prevalence in the U.S., U.K. and other countries has been climbing steadily. (K. L. Wallace et al., "Increasing Prevalence of Gout and Hyperuricemia over 10 Years Among Older Adults in a Managed Care Population." Journal of Rheumatology 2004; 31: 1582-1587). More recent data suggest that far more than 5 million Americans now have diagnosable gout. (E. Krishnan et al., "Gout in Ambulatory Care Settings in the United States." Journal of Rheumatology 2008; 35(3): 498-501).

Hyperuricemia and gout are particularly significant issues in organ transplant recipients (Stamp, L., et al, "Gout in solid organ transplantation: a challenging clinical problem", Drugs (2005) 65(18): 2593-2611). Uric acid is often elevated in patients with renal transplants, and common immunosuppressive drugs such as cyclosporine can cause particularly severe hyperuricemia. In transplant patients, allopurinol is contra-indicated due to interactions with some immunosupressants such as azathioprine, and due to bone marrow failure caused by the combination. Furthermore, elevated uric acid may contribute to graft failure (Armstrong, K. A. et al., "Does Uric Acid Have a Pathogenetic Role in Graft Dysfunction and Hypertension in Renal Transplant Patients?" Transplantation (2005) 80(11): 1565-1571). Therefore, there is a particularly acute need for safe agents that reduce hyperuricemia in transplant recipients.

Diseases related to elevated soluble uric acid often involve vascular problems: hypertension (Sundstrom et al., Relations of serum uric acid to longitudinal blood pressure tracking and hypertension incidence. Hypertension. 45(1):28-33, 2005), prehypertension (Syamela, S. et al., Association between serum uric acid and prehypertension among US adults. J. Hypertens. 25 (8) 1583-1589, (2007), atherosclerosis (Ishizaka et al., Association between serum uric acid, metabolic syndrome, and carotid atherosclerosis in Japanese individuals. Arterioscler Thromb Vasc Biol. (5):1038-44, 2005), peripheral artery disease (Shankar, A. et al., Association between serum uric acid level and peripheral artery disease. Atherosclerosis doi 10: 1016, 2007), vascular inflammation (Zoccali et al., Uric acid and endothelial dysfunction in essential hypertension. J Am Soc Nephrol. 17(5):1466-71, 2006), heart failure (Strasak, A. M. et al., Serum uric acid and risk of cardiovascular mortality: A prospective, long-term study of 83,683 Austrian men, Clin Chem. 54 (2) 273-284, 2008; Pascual-Figal, Hyperuricaemia and long-term outcome after hospital discharge in acute heart failure patients. Eur J Heart Fail. 2006 Oct. 23; [Epub ahead of print]; Cengel, A., et al., "Serum uric Acid Levels as a Predictor of In-hospital Death in Patients Hospitalized for Decompensated Heart Failure." Acta Cardiol. (October 2005) 60(5): 489-492), myocardial infarctions (Strasak, A. M. et al.; Bos et al., Uric acid is a risk factor for myocardial infarction and stroke: the Rotterdam study. Stroke. 2006 June; 37(6):1503-7), renal dysfunction (Cirillo et al., Uric Acid, the metabolic syndrome, and renal disease. J Am Soc Nephrol. 17(12 Suppl 3):5165-8, 2006; Z. Avram and E. Krishnan, Hyperuricemia—where nephrology meets rheumatology. Rheumatology (Oxford), 47(7): 960-964, 2008), and strokes (Bos et al., 2006). Uric acid directly causes endothelial dysfunction (Kanellis, et al., Uric acid as a mediator of endothelial dysfunction, inflammation, and vascular disease. Semin Nephrol. 25(1):39-42, 2005; Khosla et al, Hyperuricemia induces endothelial dysfunction. Kidney Int. 67(5):1739-42, 2005). In children and adolescents, early-onset essential hypertension is associated with elevated serum uric acid, and reduction of uric acid with allopurinol reduces blood pressure in these patients (Feig and Johnson, The role of uric acid in pediatric hypertension. J Ren Nutrition 17(1): 79-83, 2007; D. I. Feig et al., Effect of allopurinol on blood pressure of adolescents with newly diagnosed essential hypertension. JAMA 300(8): 924-932, 2008. Feig et al. also state that this is a new therapeutic approach but that the side effects of existing drugs to lower uric acid may limit or prevent their use. Hyperuricemia is an independent risk factor in all of these conditions.

Elevated soluble uric acid is also associated with or directly induces inflammatory responses. For example, uric acid is transported into vascular smooth muscle cells via organic acid transporters, especially the urate transporter URAT1, and then stimulates vascular smooth muscle cells to produce C-reactive protein, MCP-1 and other cytokines, thereby stimulating proliferation and other changes associated with atherosclerosis (Price et al., Human vascular smooth muscle cells express a urate transporter. J Am Soc Nephrol. 17(7): 1791-5, 2006; Kang et al., Uric acid causes vascular smooth muscle cell proliferation by entering cells via a functional urate transporter. Am J. Nephrol. 2005 25(5):425-33 (2005); Yamamoto et al., Allopurinol reduces neointimal hyperplasia in the carotid artery ligation model in spontaneously hypertensive rats. Hypertens. Res. 29 (11) 915-921, 2006), stimulates human mononuclear cells to produce IL-1β, IL-6 and TNF-α, causes marked increases in TNF-α when infused into mice, activates endothelial cells and platelets, and increases platelet adhesiveness (Coutinho et al., "Associations of Serum Uric Acid with Markers of Inflammation, Metabolic Syndrome, and Subclinical Coronary Atherosclerosis", Amer. J. Hypertens. (2007) 20: 83-89; Levya, F., et al., "Uric Acid in Chronic Heart Failure: A Marker of Chronic Inflammation", Eur. Heart J. (1998) 19(12): 1814-1822.). Uric acid has also been shown to inhibit bioavailability of endothelial nitric oxide and activate the renin-angiotensin system. (T. S. Perlstein et al., Uric acid and the state of the intrarenal renin-angiotensin system in humans. Kidney International. 66:1465-1470, 2004). Inokuchi et al. have shown that Interleukin 18 (IL-18) and other inflammatory agents reflect local inflammation associated with gout and that urate crystals accelerate activation of IL-18 (T. Inokuchi et al., Plasma IL-18 and other inflammatory cytokines in patients with gouty arthritis and monosodium urate monohydrate crystal-induced secretion of IL-18. Cytokine. 33(1): 21-27, 206), which appears to have a causative role in renal failure. IL-18 and other cytokines are also significantly elevated in people who do not have gout per se but who merely have elevated uric acid levels (C. Ruggiero et al. Uric acid and inflammatory markers. (C. Ruggiero et al., Uric acid and inflammatory markers. European Heart Journal. 27: 1174-1181, 2006).

Hyperuricemia is also associated with cognitive impairment and other forms of central nervous system dysfunction. (Schretlen, D. J. et al., "Serum Uric Acid and Cognitive Function in Community-Dwelling Older Adults", Neuropsychology (January 2007) 21(1): 136-140; Watanabe, S., et al., "Cerebral Oxidative Stress and Mitochondrial Dysfunction in Oxonate-Induced Hyperuricemic Mice", J. Health Science (2006) 52: 730-737).

Elevated serum uric acid levels are also associated with increased risk of cancer and cancer mortality. (Strasak, A M et al. (2007) Serum uric acid and risk of cancer mortality in a large prospective male cohort. Cancer Causes Control 18 (9) 1021-1029; Strasak, A M et al. (2007) The role of serum uric acid as an antioxidant protecting against cancer: prospective study in more than 28,000 older Austrian women. Annals Oncol 18 (11) 1893-1897; Jee, S A et al. (2004) Serum uric acid and risk of death from cancer, cardiovascular disease or all causes in men Eur. J. Cardiovascular Prev. Rehab. 11 (3) 185-191)

Elevated levels of uric acid are associated with prediabetes, insulin resistance, the development of Type 2 diabetes, and an increased probability of a variety of undesirable conditions in people with diabetes, such as peripheral artery disease, strokes, and increased mortality risk, (Ioachimescu, A. G. et al. (2007) Serum uric acid, mortality and glucose control in patients with Type 2 diabetes mellitus: a PreCIS database study Diabet. Med. 24 (12) 1369-1374; Perry, I. J. et al (1995) Prospective study of risk factors for development of non-insulin dependent diabetes in middle aged British men BMJ 310 (6979) 560-564; Chien, K-L et al. (2008) Plasma uric acid and the risk of Type 2 diabetes in a Chinese community Clin. Chem. 54 (2) 310-316; Sautin, Y. Y. et al. (2007) Adverse effects of the classic antioxidant uric acid in adipocytes: NADPH oxidase-mediated oxidative/nitrosative stress Am. J. Physiol. Cell Physiol. 293: C584-0596; Tseng, C. H. (2004) Independent association of uric acid levels with peripheral artery disease in Taiwanese patients with Type 2 diabetes Diabet. Med. 21 (7) 724-729; Lehto, S. et al. (1998) Serum uric acid is a strong predictor of stroke in patients with non-insulin dependent diabetes mellitus Stroke 29: 635-639.

Elevated levels of uric acid are a defining feature of Lesch-Nyhan Syndrome. People with sleep apnea or sleep-disordered breathing also have elevated of uric acid (Saito, H. et al., Tissue hypoxia in sleep apnea syndrome assessed by uric acid and adenosine. Chest 122: 1686-1694, 2002; Verhulst, S. L., et al., Sleep-disordered breathing and uric acid in overweight and obese children and adolescents. Chest 132: 76-80, 2007)

Elevated uric acid is associated with preeclampsia (Bainbridge, S. A. and Roberts, J. M., Uric acid as a pathogenic factor in preeclampsia. Placenta Dec. 17, 2007 epub ahead of print).

"Uric acid is a major contributor of the inflammatory response triggered by *P. falciparum* in human peripheral blood mononuclear cells . . . [T]he inflammatory reaction induced by *P. falciparum* is considered a major cause of malaria pathogenesis . . . " PLoS ONE 2009; 4(4):e5194. Epub 2009 Apr. 17.

There is a significant medical need for new medications that can safely, conveniently and effectively treat and prevent disorders related to elevation of blood uric acid, whether such diseases are due to crystallization of uric acid or to effects of supranormal (whether by an individual or a population-based standard) levels of soluble uric acid.

SUMMARY OF THE INVENTION

This invention provides a compound represented by Formula

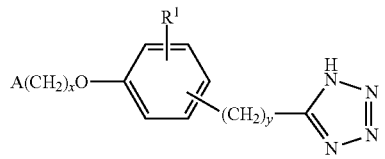

(I)

In Formula I, x is 1 or 2; y is 0, 1, 2 or 3; $R^1$ is selected from the group consisting of hydrogen, alkyl having 1 or 2 carbon atoms, hydroxy, alkoxy having 1 or 2 carbon atoms, fluoro, chloro, bromo, and amino. A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy; or cycloalkyl having from 3 to 6 ring atoms wherein the cycloalkyl is unsubstituted or one or two ring carbons are independently mono-substituted by methyl or ethyl; or a 5 or 6 membered heteraromatic ring having 1 or 2 ring heteroatoms selected from N, S and O and the heteroaromatic ring is covalently bound to the remainder of the compound by a ring carbon.

This invention provides a method of reducing the uric acid concentration in blood of, or increasing uric acid excretion from, a mammalian subject, comprising administering to the subject a compound of this invention in an amount effective to reduce the uric acid concentration in blood of, or increase uric acid excretion from, the subject. This invention provides a compound of this invention for use in reducing the uric acid concentration in blood of, or increasing uric acid excretion from, a mammal. This invention provides the use of a compound of this invention in the manufacture of a medicament for reducing the uric acid concentration in blood of, or increasing uric acid excretion from, a mammal. This invention provides a pharmaceutical composition for use in reducing the uric acid concentration in blood of, or increasing uric acid excretion from, a mammalian subject comprising a compound of this invention in an amount effective to reduce the uric acid concentration in blood of, or increase uric acid excretion from, the subject. This invention provides a kit comprising one or more unit oral doses of a compound of this invention, and instructions for administering the compound to reduce the uric acid concentration in blood of, or increasing uric acid excretion from, a mammalian subject.

Reducing uric acid as described herein can be used to treat or prevent a variety of conditions including gout (any or all of: asymptomatic gout, acute gouty arthritis, intercritical gout, and chronic tophaceous gout), hyperuricemia, elevated levels of uric acid that do not meet the levels customarily justifying a diagnosis of hyperuricemia, renal dysfunction, kidney stones, cardiovascular disease, risk for developing cardiovascular disease and other consequences of hyperuricemia, cognitive impairment, early-onset essential hypertension, and *Plasmodium falciparum*-induced inflammation.

This invention is based on the observation that compounds of this invention inhibited URAT1 in vitro, as shown in Example 7. Inhibition of URAT1 is an established in vitro model for lowering uric acid in vivo.

DETAILED DESCRIPTION OF THE INVENTION

Definitions

Figure 1:
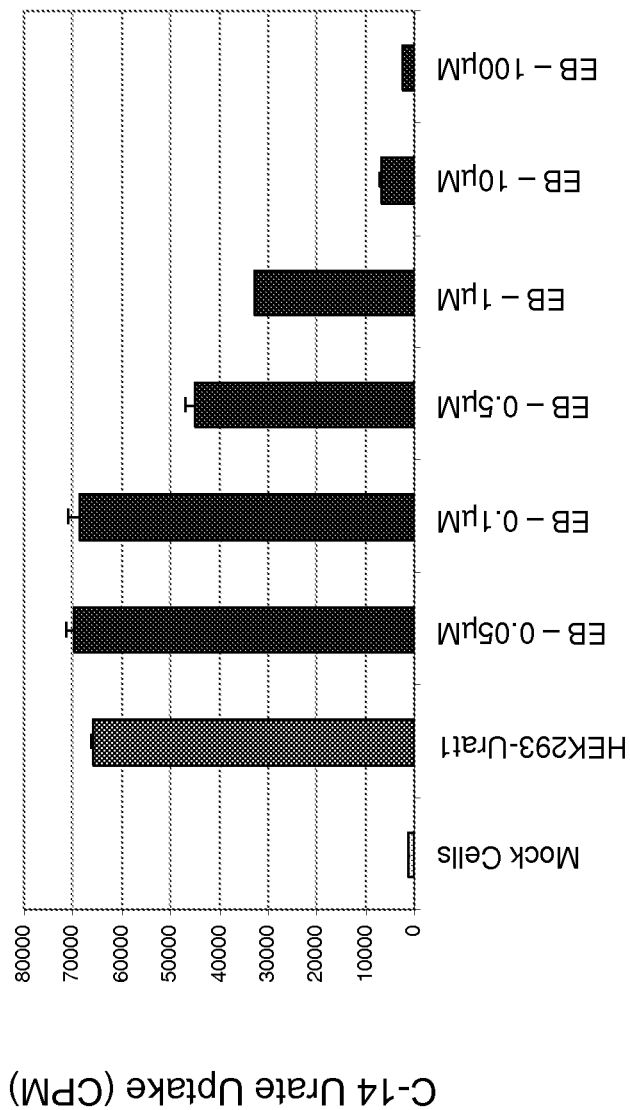
FIG. 1: Concentration-Dependent Inhibitory Effects of Compound EB on $^{14}$C-urate uptake in hURAT1-HEK Cells
Figure 2:
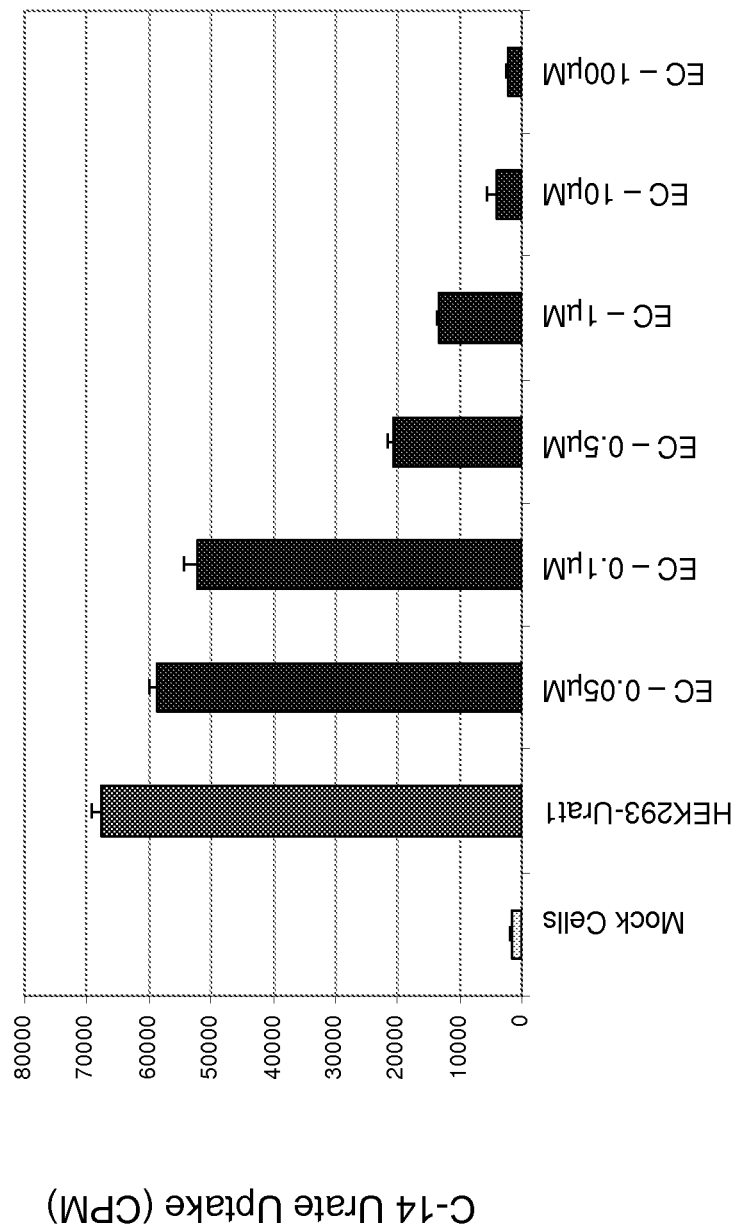
FIG. 2: Concentration-Dependent Inhibitory Effects of Compound EC on $^{14}$C-urate uptake in hURAT1-HEK Cells

A 1H-tetrazolyl-5-yl moiety and the corresponding 2H-tetrazolyl-5-yl moiety can exist as tautomers. In this document compounds are named and structural formulas are written with reference to the 1H-tautomer. All such references are to be understood as including both tautomeric forms. Thus, for example, "5-(3-(2,6-Dimethylbenzyloxy)phenyl)-1H-tetrazole" includes both 5-(3-(2,6-Dimethylbenzyloxy)phenyl)-1H-tetrazole and 5-(3-(2,6-Dimethylbenzyloxy)phenyl)-2H-tetrazole. And Formula I includes both Formula I as depicted above and its 2H-tetrazolyl-5-yl tautomeric form depicted in Formula I' below.

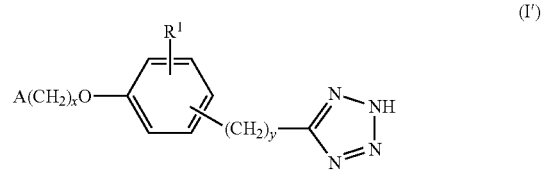

(I')

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and an alkyl having four carbon atoms can be n-butyl, 1-methylpropyl, 2-methylpropyl or t-butyl.

As used herein the term "halo" refers to one or more of fluoro, chloro, bromo and iodo.

As used herein the term "perfluoro" as in perfluoromethyl or perfluoromethoxy, means that the group in question has fluorine atoms in place of all of the hydrogen atoms. Certain chemical Compounds are referred to herein by their chemical name or by the two-letter code shown below. Compounds EB through EI and compound BD are included within the scope of Formula I shown above.

EB 5-(3-(2,6-Dimethylbenzyloxy)phenyl)-1H-tetrazole
EC 5-(3-(2,6-Dimethylbenzyloxy)benzyl)-1H-tetrazole
ED 5-(3-(2,6-Dimethylbenzyloxy)-4-methoxybenzyl)-1H-tetrazole
EF 5-(3-(2,6-Dimethylbenzyloxy)phenethyl)-1H-tetrazole
EG 5-(3-(2,6-Dimethylbenzyloxy)-4-methylbenzyl)-1H-tetrazole
BD 5-(4-(2,6-Difluorobenzyloxy)benzyl)-1H-tetrazole
EH 5-(3-(2,6-Dimethylbenzyloxy)-2-methylbenzyl)-1H-tetrazole
EI 5-(3-(2,6-Dimethylbenzyloxy)-2-methoxybenzyl)-1H-tetrazole As used herein the transitional term "comprising" is open-ended. A claim utilizing this term can contain elements in addition to those recited in such claim.

As used in the claims the word "or" means "and/or" unless such reading does not make sense in context. So for example the phrase "reducing the uric acid concentration in blood of or increasing uric acid excretion from, a mammalian subject" is equivalent to "reducing the uric acid concentration in blood of and/or increasing uric acid excretion from, a mammalian subject.

Compounds of the Invention

In an embodiment of the compound, method, use or pharmaceutical composition described in the Summary above, the compound is represented by Formula XLVI.

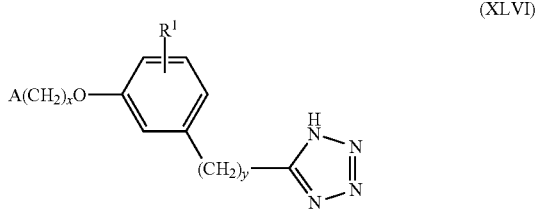

wherein x, y, $R^1$ and A are as described above for Formula I.

In a further embodiment of this invention the compound is represented by Formula XLVII

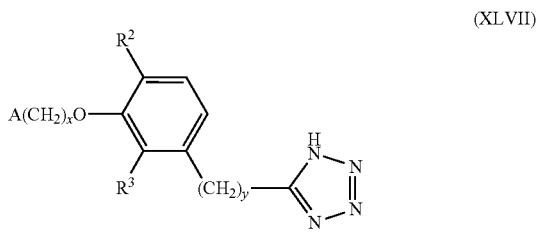

wherein x, y, and A are as described above for Formula I; and one of $R^2$ and $R^3$ is hydrogen and the other is selected from the group consisting of hydrogen, alkyl having 1 or 2 carbon atoms, hydroxy, alkoxy having 1 or 2 carbon atoms, fluoro, chloro, bromo, and amino.

In an embodiment of this invention, in Formula I, XLVI or XLVII, x is 1. In another embodiment A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy. In a more specific embodiment A is 2,6-dimethylphenyl or 2,6-difluorophenyl. Preferably A is 2,6-dimethylphenyl.

In embodiment of this invention the compound is represented by Formula XLVIII

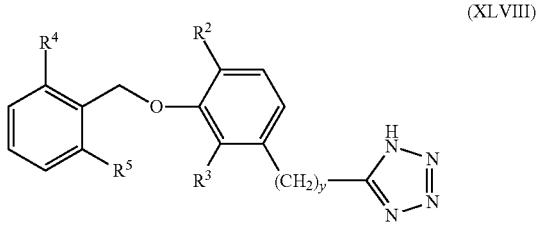

wherein y is 0, 1, 2 or 3; one of $R^2$ and $R^3$ is hydrogen and the other is selected from the group consisting of hydrogen, alkyl having 1 or 2 carbon atoms, hydroxy, alkoxy having 1 or 2 carbon atoms, fluoro, chloro, bromo, and amino; and $R^4$ and $R^5$ are independently selected from the group consisting of methyl, fluoro and chloro.

In an embodiment of this invention, in Formula I, XLVI, XLVII or XLVIII, y is 0, 1 or 2. In an embodiment of this invention, in Formula XLVII or XLVIII, $R^3$ is hydrogen and $R^2$ is selected from the group consisting of hydrogen, alkyl having 1 or 2 carbon atoms, hydroxy, alkoxy having 1 or 2 carbon atoms, fluoro, chloro, bromo, and amino. In a more specific embodiment $R^3$ is hydrogen and $R^2$ is selected from the group consisting of hydrogen, methyl, and methoxy. In a different embodiment of this invention, in Formula XLVII or XLVIII, $R^2$ is hydrogen and $R^3$ is selected from the group consisting of, alkyl having 1 or 2 carbon atoms, hydroxy, alkoxy having 1 or 2 carbon atoms, fluoro, chloro, bromo, and amino. In a more specific embodiment $R^2$ is hydrogen and $R^3$ is selected from the group consisting of methyl and methoxy. In a further embodiment of Formula XLVIII, both of $R^4$ and $R^5$ are methyl or both are fluoro. Preferably both are methyl.

In specific embodiments of this invention the compound is selected from the group consisting of: 5-(3-(2,6-Dimethylbenzyloxy)phenyl)-1H-tetrazole; 5-(3-(2,6-Dimethylbenzyloxy)benzyl)-1H-tetrazole; 5-(3-(2,6-Dimethylbenzyloxy)-4-methoxybenzyl)-1H-tetrazole; 5-(3-(2,6-Dimethylbenzyloxy)phenethyl)-1H-tetrazole; 5-(3-(2,6-Dimethylbenzyloxy)-4-methylbenzyl)-1H-tetrazole; 5-(4-(2,6-Difluorobenzyloxy)benzyl)-1H-tetrazole; 5-(3-(2,6-Dimethylbenzyloxy)-2-methylbenzyl)-1H-tetrazole; and 5-(3-(2,6-Dimethylbenzyloxy)-2-methoxybenzyl)-1H-tetrazole.

In an embodiment of the compound of this invention, the compound is in substantially (at least 98%) pure form.

Reaction Schemes

The compound of formula I where x is 1 or 2, y is 0 to 3, $R^1$ is hydrogen, fluoro, bromo, chloro, alkoxy having from 1 to 2 carbon atoms or alkyl having from 1 to 2 carbon atoms, i.e. compounds of formula:

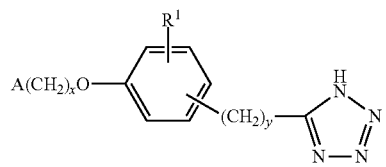

wherein A is described as above, can be prepared via reaction of scheme 1. In the reaction of scheme 1, A, x, y, and $R^1$ are as above. L is a leaving group.

The compound of formula II can be converted to the compound of formula V via reaction of step (a) using Mitsunobu condensation of II with III using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (a).

The compound of formula V can also be prepared by etherifying or alkylating the compound of formula II with the compound of formula IV as in reaction of step (a) by using suitable base for example potassium carbonate, triethylamine, pyridine and the like. The reaction is carried out in nonprotic solvents for example N,N-dimethylformamide, acetonitrile, dichloromethane and the like. In the compound of formula IV, L, include but are not limited to mesyloxy, tosyloxy, chloro, bromo, iodo, and the like. Any conventional method of etherifying of a hydroxyl group by reaction with a halide or leaving group can be utilized to carry out the reaction of step (a).

The compound of formula V can be converted to the compound of formula I via reaction of step (b) by reacting the nitrile with an azide for example trimethylsilyl azide or with metal azide for example sodium azide, potassium azide, lithium azide preferred azide being sodium azide in the presence of lewis acid for example zinc chloride, magnesium chloride, aluminum chloride, tin tetrachloride and the like. The reaction is carried out in the solvent for example N,N-dimethylformamide at the temperature ranging from 80° C. to 145° C. from 6 to 60 hours. The ideal reaction utilizes reacting nitrile with sodium azide/ammonium chloride/N,N-dimethylformamide at 120° C. for 24 hours. The products can be isolated and purified by techniques such as extraction, evaporation, chromatography, and recrystallization.

If A is phenyl substituted by 1 or 2 groups of hydroxyl groups, it is generally preferred to protect the hydroxyl groups. The suitable protecting group can be described in the Protective Groups in Organic Synthesis by T. Greene. The protecting group can be deprotected after the reaction of step (b) utilizing suitable deprotecting reagents such as those described in Protective Groups in Organic Synthesis by T. Greene.

Reaction Scheme 1

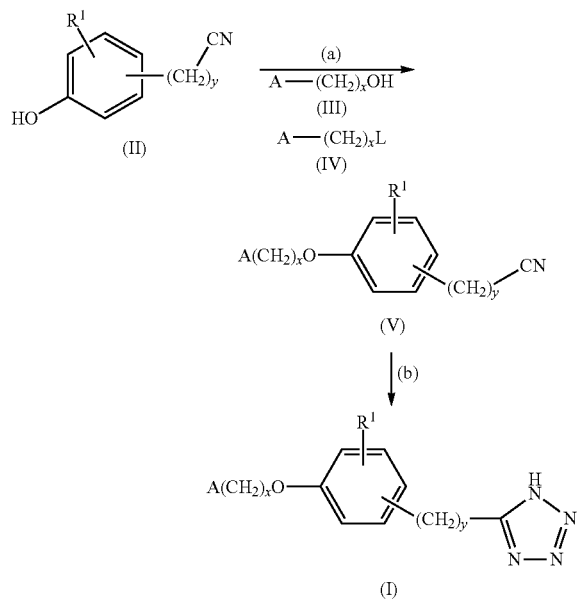

The compound of formula I where x is 1 or 2, y is 0 to 3, $R^1$ is hydroxyl, i.e. compounds of formula:

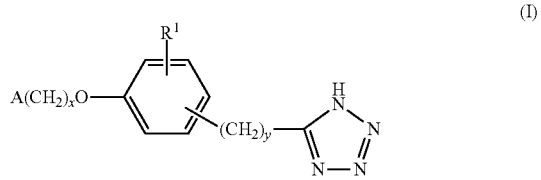

wherein A is described as above, can be prepared via reaction of scheme 2. In the reaction of scheme 2, A, x, and y are as above.

The compound of formula V can be converted to the compound of formula VI via reaction of step (c) by treating the compound of formula V with boron tribromide or boron trichloride using solvent for example dichloromethane for 4 to 48 hours at the temperature ranges from −72° C. to 0° C. Any of the conditions conventional in such demethylation reactions can be utilized to carry out the reaction of step (c).

The compound of formula VI can be converted to the compound of formula I where $R^1$ is hydroxyl via reaction of step (d) in the same manner as described hereinbefore in the reaction of step (b). The products can be isolated and purified by techniques such as extraction, evaporation, chromatography, and recrystallization.

Reaction Scheme 2

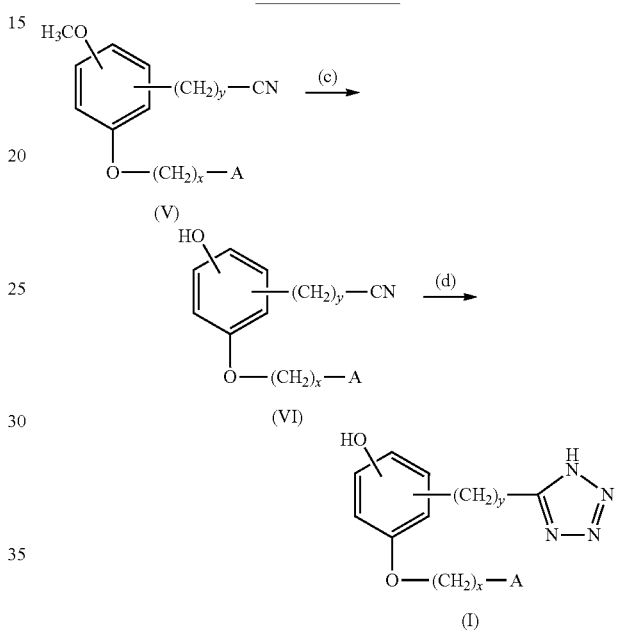

The compound of formula I where x is 1 or 2, y is 0 to 3, $R^1$ is amino, i.e. compounds of formula:

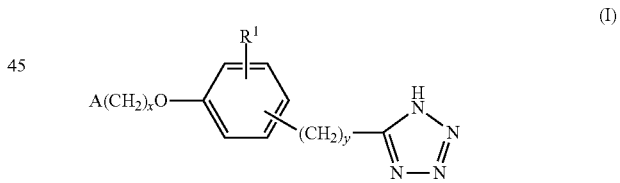

wherein A is described as above, can be prepared via reaction of scheme 3. In the reaction of scheme 3, A, x, and y are as above. P is a protecting group.

The compound of formula VII can be converted to the compound of formula VIII via the reaction of step (e) in the same manner as described hereinbefore in the reaction of step (a). The compound of VIII can be converted to the compound of formula IX via reaction of step (f) by reducing the nitro group to amine. The reducing agents can be metals for example Zn, Sn, or Fe and the like and acid. The nitro group can also be reduced by catalytic hydrogenation to give amine. The preferred reduction method is catalytic hydrogenation. Any of the conditions conventional in such reductions reactions can be utilized to carry out the reaction of step (f).

The compound of formula IX can be converted to the compound of formula X via reaction of step (g) by protecting the amino group. The suitable protecting group can be described in the Protective Groups in Organic Synthesis by T.

Greene. The compound of formula X can be converted to the compound of formula XI via reaction of step (h) in the same manner as described hereinbefore in the reaction of step (b). The compound of formula XI can be converted to the compound of formula I where $R^1$ is amino via reaction step of (i) by deprotecting the amino protecting group. The suitable deprotecting reagents can be described in Protective Groups in Organic Synthesis by T. Greene. The products can be isolated and purified by techniques such as extraction, evaporation, chromatography, and recrystallization.

carbon atoms. P is a hydroxy protecting group. $R^2$ is alkyl group having 1 to 2 carbon atoms. Y is a halide.

The compound of formula XII can be converted to the compound of formula XIII via reaction of step (j) by first protecting the carboxylic and hydroxy groups by utilizing suitable protecting groups such as those described in Protective Groups in Organic Synthesis by T. Greene.

The compound of formula XIII can be reduced to the compound of formula XIV where $R^3$ is hydrogen, fluoro, bromo, chloro, alkoxy having from 1 to 2 carbon atoms or Reaction Scheme 3

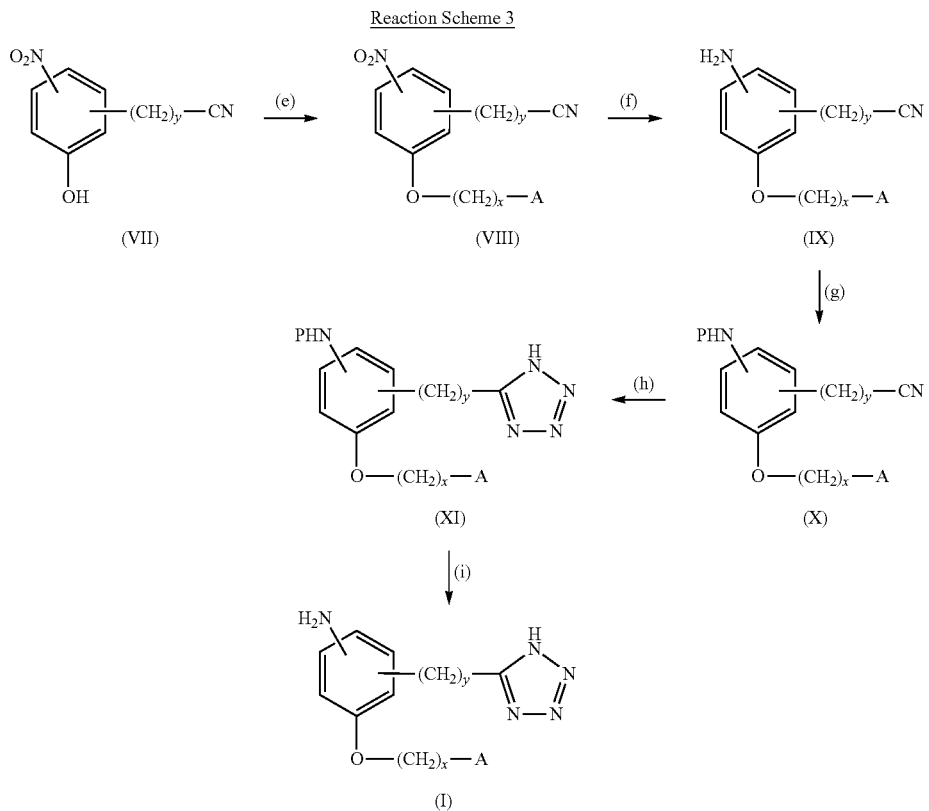

The compound of formula II where y is 1 to 3, $R^1$ is hydrogen, fluoro, bromo, chloro, alkoxy having from 1 to 2 carbon atoms or alkyl having from 1 to 2 carbon atoms, i.e. compounds of formula:

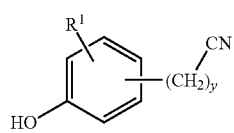

(II)

and the compound of formula VII where y is 1 to 3, i.e. compounds of formula:

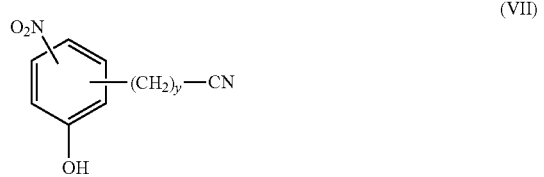

(VII)

can be prepared via reaction of scheme 4. In the reaction of scheme 4, $R^3$ is hydrogen, fluoro, bromo, chloro, nitro, alkoxy having from 1 to 2 carbon atoms or alkyl having from 1 to 2 alkyl having from 1 to 2 carbon atoms by utilizing conventional reducing reagent that converts ester group to an alcohol via reaction of step (k). In carrying out this reaction it is generally preferred but not limited to utilize lithium aluminum hydride. The reaction is carried out in a suitable solvent such as tetrahydrofuran and the like. Any of the conditions conventional in such reduction reactions can be utilized to carry out the reaction of step (k).

The compound of formula XIII can be reduced to the compound of formula XIV where $R^3$ is nitro by utilizing reducing reagent that converts ester to an alcohol but does not reduce nitro group for example $BH_3$-THF, $NaBH_4$—$AlCl_3$ and the like. Any of the conditions conventional in such reduction reactions can be utilized to carry out the reaction of step (k). The compound of formula XIV can be converted to the compound of formula XV by displacing hydroxy group with a halogen preferred halogen being bromo or chloro. Appropriate halogenating reagents include but are not limited to thionyl chloride, oxalyl chloride, bromine, phosphorous tribromide, carbon tetrabromide and the like. Any conditions conventional in such halogenation reactions can be utilized to carry out the reaction of step (1).

The compound of formula XV can be converted to the compound of formula XVI by reacting XV with an alkali metal cyanide for example sodium or potassium cyanide or copper cyanide. The reaction can be carried out in a suitable solvent for example dimethyl sulfoxide, N,N-dimethylformamide and the like. Any of the conditions conventionally used in the preparation of nitriles from halides can be utilized to carry out the reaction of step (m).

The compound of formula XVI can be converted to the compound of formula XVII via reaction of step (n) by removal of hydroxy protecting group utilizing suitable deprotecting reagents such as those described in Protective Groups in Organic Synthesis by T. Greene. The compound of formula XVII is the compound of formula II where y is 1 and $R^1$ is hydrogen, fluoro, bromo, chloro, alkoxy having from 1 to 2 carbon atoms or alkyl having from 1 to 2 carbon atoms. The compound of formula XVII is also compound of formula VII where y is 1 and $R^3$ is nitro. The compound of formula XVI can be converted to the compound of formula XVIII via reaction step (o) by acid or base hydrolysis. In carrying out this reaction, it is generally preferred to utilize basic hydrolysis, for example aqueous sodium hydroxide in ethanol and the like. Any of the conditions conventional in the hydrolysis of nitriles to a carboxylic acids can be utilized to carry out the reaction of step (o).

The compound of formula XVIII can be reduced to give the compound of formula XIX via reaction of step (p). This reaction can be carried out in the same manner as described hereinbefore in the reaction of step (k). The compound of formula XIX can be converted to the compound of formula XX via reaction of step (q) in the same manner as described hereinbefore in the reaction of step (l). The compound of formula XX can be converted to the compound of formula XXI via reaction of step (r) in the same manner as described hereinbefore in the reaction of step (m). The compound of formula XXI can be converted to the compound of formula XXII via reaction of step (s) in the same manner as described hereinbefore in the reaction of step (n).

The compound of formula XXII is the compound of formula II where y is 2 and $R^1$ is hydrogen, fluoro, bromo, chloro, alkoxy having from 1 to 2 carbon atoms or alkyl having from 1 to 2 carbon atoms. The compound of formula XVII is also compound of formula VII where y is 2 and $R^3$ is nitro.

The compound of formula XXI can be hydrolyzed in the same manner as described hereinbefore in the reaction of step (o) to give the compound of formula XXIII via the reaction of step (t).

The compound of formula XXIII can be reduced to give the compound of formula XXIV via reaction of step (u). This reaction can be carried out in the same manner as described hereinbefore in the reaction of step (k). The compound of formula XXIV can be converted to the compound of formula XXV via reaction of step (v) in the same manner as described hereinbefore in the reaction of step (l). The compound of formula XXV can be converted to the compound of formula XXVI via reaction of step (w) in the same manner as described hereinbefore in the reaction of step (m). The compound of formula XXVI can be converted to the compound of formula XXVII via reaction of step (x) in the same manner as described hereinbefore in the reaction of step (n). The compound of formula XXVII is the compound of formula II where y is 3 and $R^1$ is hydrogen, fluoro, bromo, chloro, alkoxy having from 1 to 2 carbon atoms or alkyl having from 1 to 2 carbon atoms. The compound of formula XXVII is also compound of formula VII where y is 3 and $R^3$ is nitro.

The products can be isolated and purified by techniques such as extraction, evaporation, chromatography, and recrystallization.

Reaction Scheme 4

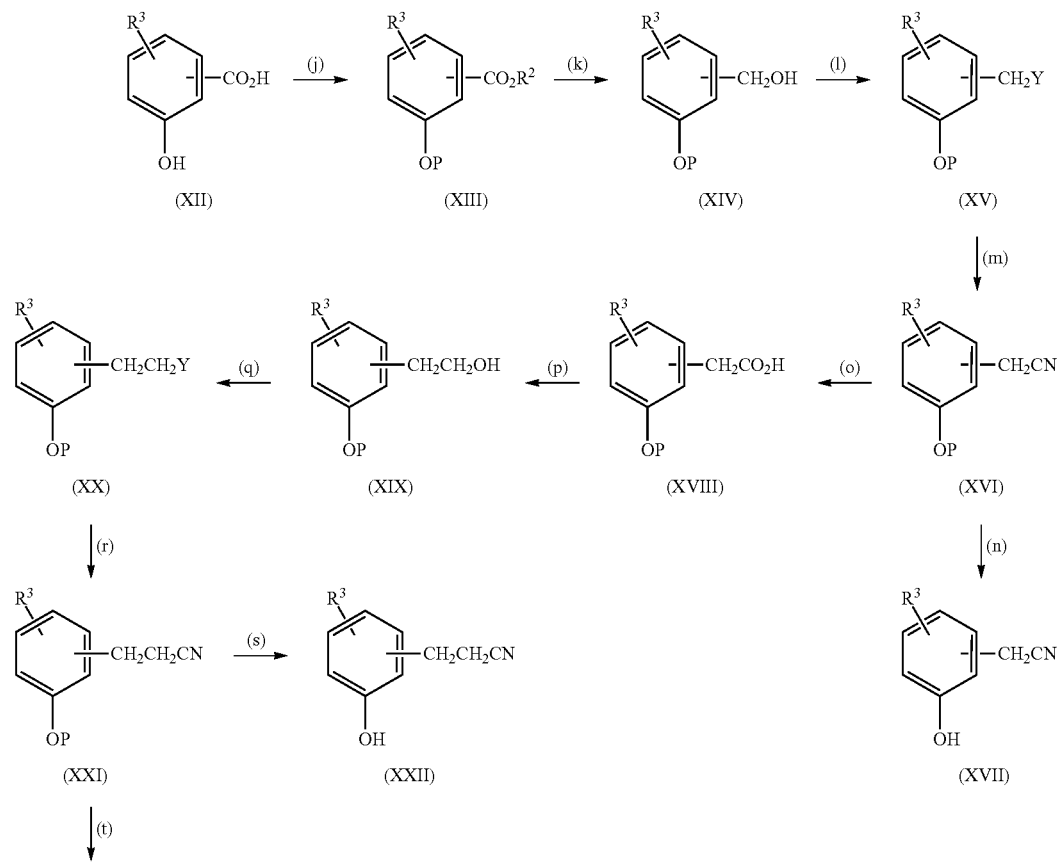

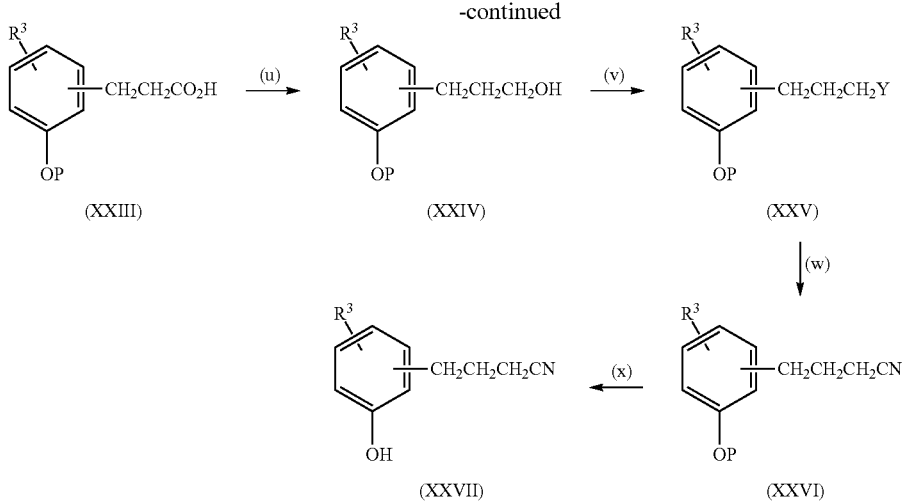

The compound of formula II where y is 0, $R^1$ is hydrogen, fluoro, bromo, chloro, alkoxy having from 1 to 2 carbon atoms or alkyl having from 1 to 2 carbon atoms, i.e. compounds of formula:

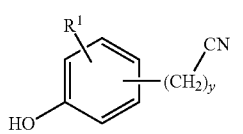

(II)

and the compound of formula VII where y is 0, i.e. compounds of formula:

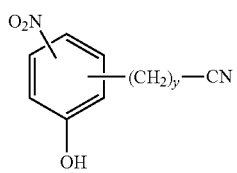

(VII)

can be prepared via reaction of scheme 5. In the reaction of scheme 5, $R^3$ is hydrogen, nitro, fluoro, bromo, chloro, alkoxy having from 1 to 2 carbon atoms or alkyl having from 1 to 2 carbon atoms. P is a hydroxy protecting group. $R^2$ is alkyl group having 1 to 2 carbon atoms. $R^4$ is H, chloro or bromo.

The compound of formula XXVIII can be converted to the compound of formula XXIX via reaction of step (y) by first protecting the hydroxy group by utilizing suitable protecting groups such as those described in Protective Groups in Organic Synthesis by T. Greene and then hydrolyzing ester to give the compound of formula XXIX where $R^4$ is H.

The compound of formula XXVIII can be converted to the compound of formula XXIX where $R^4$ is chloro or bromo by reacting the compound of formula from step (y) with halogenating reagent for example thionyl chloride, phosphorous pentachloride, phosphorous trichloride, bromine, carbon tetrabromide and the like. Any of the conditions conventional in such halogenations reactions of carboxylic acids can be utilized to carry out the reaction of step (z).

The compound of formula XXIX can be converted to the compound of formula XXX via reaction of (a') by reacting with ammonia directly or by first treating the compound of formula XXIX with coupling reagent for example dicyclohexylcarbodiimide, benzotriazolyloxy)tris(dimethylamino) phosphonium hexafluorophosphate and then reacting with ammonia and the like. Any of the conditions conventional in acylation of ammonia can be utilized to carry out the reaction of step (a'). The compound of formula XXX can be converted to the compound of formula XXXI via reaction of step (b') by dehydration utilizing reagents for example thionyl chloride, phosphorous pentoxide, phosphorous pentachloride, phosphorous oxychloride, carbon tetrachloride-triphenylphosphine, cyanuric chloride, and the like. The reaction is carried out either neat or in suitable solvent for example N,N-dimethylformamide and the like. Any of the conditions conventional in such dehydration reaction can be utilized to carry out the reaction of step (b').

The compound of formula XXXI can be converted to the compound of formula XXXII via reaction of step (c') by removal of hydroxy protecting group utilizing suitable deprotecting reagents such as those described in Protective Groups in Organic Synthesis by T. Greene. The compound of formula XXXII is the compound of formula II where y is 0 and $R^1$ is hydrogen, fluoro, bromo, chloro, alkoxy having from 1 to 2 carbon atoms or alkyl having from 1 to 2 carbon atoms. The compound of formula XXXII is also compound of formula VII where y is 0 and $R^3$ is nitro. The products can be isolated and purified by techniques such as extraction, evaporation, chromatography, and recrystallization.

Reaction Scheme 5

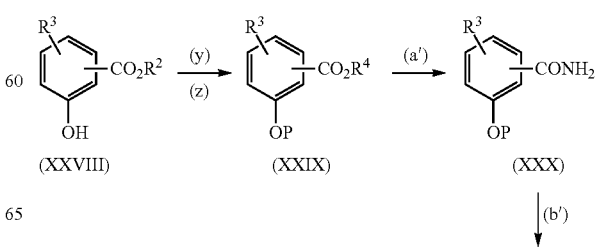

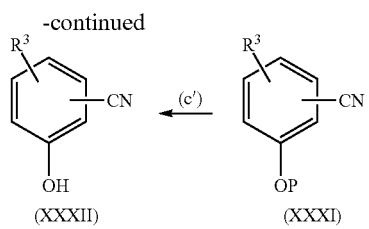

The compound of formula III, where x is 1 or 2, i.e. compounds of formula:

A-(CH$_2$)$_x$OH and the compound of formula IV, where x is 1 or 2, i.e. compounds of formula:

A-(CH$_2$)$_x$L

The compound of formula XXXVII can be reduced to give the compound of formula XXXVIII via reaction of step (h'). This reaction can be carried out in the same manner as described hereinbefore in the reaction of step (d'). The compound of formula XXXVIII is the compound of formula III where x is 2.

The compound of formula XXXVIII can be converted to the compound of formula XXXIX via reaction of step (i') in the same manner as described hereinbefore in the reaction of step (e'). The compound of formula XXXIX is the compound of formula IV where x is 2.

The products can be isolated and purified by techniques such as extraction, evaporation, chromatography, and recrystallization. If A is phenyl substituted by 1 or 2 groups of hydroxyl, it is generally preferred to protect the hydroxyl group of the compound of formula XXXIII. The suitable protecting group can be described in the Protective Groups in Organic Synthesis by T. Greene.

Reaction Scheme 6

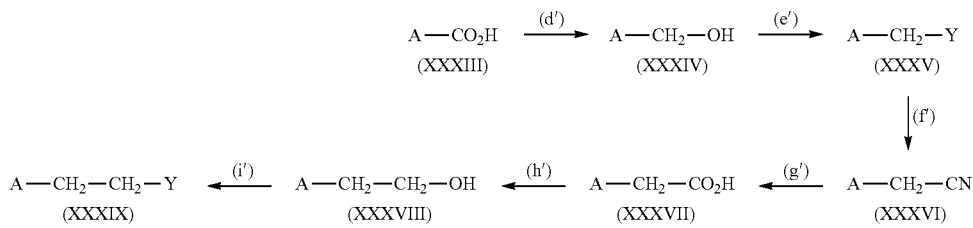

can be prepared via reaction of scheme 6. In the reaction of scheme 6, A is described as above. L is a leaving group or halide. The compound of formula XXXIII can be reduced to the compound of formula XXXIV via reaction of step (d'). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (d').

The compound of formula XXXIV is the compound of formula III where x is 1.

The compound of formula XXXIV can be converted to the compound of formula XXXV by displacing hydroxyl group with a leaving group or halide preferred group being bromo or chloro. Appropriate reagents for halogenation include but are not limited to thionyl chloride, oxalyl chloride, bromine, phosphorous tribromide, carbon tetrabromide and the like. The leaving groups include tosylate, mesylate and the like. Any conditions conventional in such reactions can be utilized to carry out the reaction of step (e'). The compound of formula XXXV is the compound of formula IV where x is 1.

The compound of formula XXXV can be converted to the compound of formula XXXVI by reacting XXXV with an alkali metal cyanide for example sodium or potassium cyanide. The reaction is carried out in a suitable solvent, such as ethanol, dimethyl sulfoxide, N,N-dimethylformamide and the like. Any of the conditions conventionally used in the preparation of nitriles can be utilized to carry out the reaction of step (f').

The compound of formula XXXVI can be converted to the compound of formula XXXVII via reaction step (g') by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (g').

The compound of formula XXVIII, where R$^3$ is hydrogen, nitro, fluoro, bromo, chloro, alkoxy having from 1 to 2 carbon atoms or alkyl having from 1 to 2 carbon atoms, R$^2$ is alkyl group having 1 to 2 carbon atoms, i.e. compounds of formula:

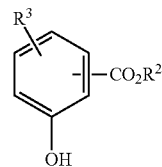

(XXVIII)

can be prepared via reaction of scheme 7. In the reaction of scheme 7, R$^2$ and R$^3$ are as above.

The compound of formula XII can be converted to the compound of formula XXVIII via reaction of step (j') by esterification of the compound of formula XII with methanol or ethanol. The reaction can be carried out either by using catalysts for example H$_2$SO$_4$, TsOH and the like or by using dehydrating agent for example dicyclohexylcarbodiimide and the like. Any of the conditions conventional in such esterification reactions can be utilized to carry out the reaction of step (j'). The product can be isolated and purified by techniques such as extraction, evaporation, chromatography, and recrystallization.

Reaction Scheme 7

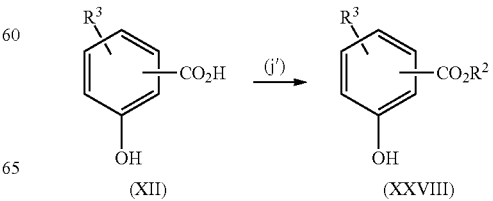

The compound of formula XII, where $R^3$ is chloro, bromo or fluoro, i.e. compounds of formula:

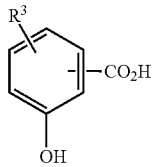

(XII)

are either commercially available or can be prepared according to the methods described in the literature as follows:
1. 3-Br or F-2-$OHC_6H_3CO_2H$
Canadian Journal of Chemistry (2001), 79(11) 1541-1545.
2. 4-Br-2-$OHC_6H_3CO_2H$
WO 9916747 or JP 04154773.
3. 2-Br-6-$OHC_6H_3CO_2H$
JP 47039101.
4. 2-Br-3-$OHC_6H_3CO_2H$
WO 9628423.
5. 4-Br-3-$OHC_6H_3CO_2H$
WO 2001002388.
6. 3-Br-5-$OHC_6H_3CO_2H$
Journal of labelled Compounds and Radiopharmaceuticals (1992), 31 (3), 175-82.
7. 2-Br-5-$OHC_6H_3CO_2H$ and 3-Cl-4-$OHC_6H_3CO_2H$
WO 9405153 and U.S. Pat. No. 5,519,133.
8. 2-Br-4-$OHC_6H_3CO_2H$ and 3-Br-4-$OHC_6H_3CO_2H$
WO 20022018323
9. 2-Cl-6-$OHC_6H_3CO_2H$
JP 06293700
10. 2-Cl-3-$OHC_6H_3CO_2H$
Proceedings of the Indiana Academy of Science (1983), Volume date 1982, 92, 145-51.
11. 3-Cl-5-$OHC_6H_3CO_2H$
WO 2002000633 and WO 2002044145.
12. 2-Cl-5-$OHC_6H_3CO_2H$
WO 9745400.

The compound of formula XII, where $R^3$ is alkoxy having from 1 to 2 carbon atoms, i.e. compounds of formula:

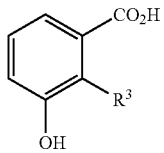

(XII)

can be prepared via the reaction of scheme 8. In the reaction of scheme 8, $R^2$ is alkyl group having from 1 to 2 carbon atoms. P is a hydroxyl protecting group. The compound of formula XL can be converted to the compound of formula XLI via reaction of step (k') by protecting phenol group by suitable protecting group. The suitable conditions for the protecting group can be described in the Protective Groups in Organic Synthesis by T. Greene.

The compound of formula XLI can be converted to the compound of formula XLII by oxidation of aldehyde to carboxylic acid. The reaction can be carried out by using suitable oxidizing reagents for example, pyridinium chlorochromate, potassium permanganate, sodium permanganate and the like. Any of the conditions suitable in such oxidation reactions can be utilized to carry out the reaction of step (l').

The compound of formula XLII can be converted to the compound of formula XII via reaction of step (m') where $R^3$ is alkoxy having 1 carbon atom by deprotection of protecting group. The suitable deprotecting conditions can be described in the Protective Groups in Organic Synthesis by T Greene.

The compound of formula XLII can be converted to the compound of formula XLIII by treating the compound of formula XLII with boron tribromide or boron trichloride using solvent for example dichloromethane for 4 to 48 hours at the temperature from −72° C. to 0° C. Any of the conditions conventional in such demethylation reactions can be utilized to carry out the reaction of step (n').

The compound of formula XLIII can be converted to the compound of formula XLIV by esterification of compound of formula XLIII with methanol or ethanol. The reaction can be carried out either by using catalysts for example $H_2SO_4$, TsOH and the like or by using dehydrating agent for example dicyclohexylcarbodiimide and the like. Any of the conditions conventional in such esterification reactions can be utilized to carry out the reaction of step (o').

The compound of formula XLIV can be converted to the compound of formula XLV by etherifying or alkylating the compound of formula XLIV with ethyl halide by using suitable base for example potassium carbonate, sodium hydride, pyridine and the like. The reaction can be carried out in conventional solvents, such as tetrahydrofuran, N,N-dimethylformamide, dichloromethane and the like. The reaction is generally carried out at temperatures from 0° C. to 40° C. Any of the conditions suitable in such alkylation reactions can be utilized to carry out the reaction of step (p').

The compound of formula XLV can be converted to the compound of formula XII via reaction of step (q') where $R^3$ is alkoxy having 2 carbon atoms by deprotection of protecting group. The suitable deprotecting conditions can be described in the Protective Groups in Organic Synthesis by T Greene. The product can be isolated and purified by techniques such as extraction, evaporation, chromatography, and recrystallization.

Reaction Scheme 8

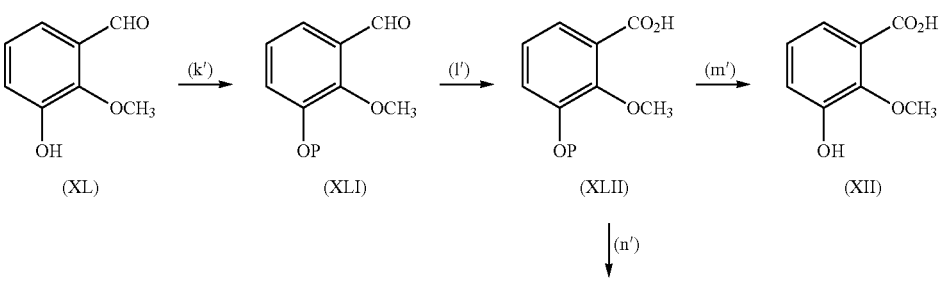

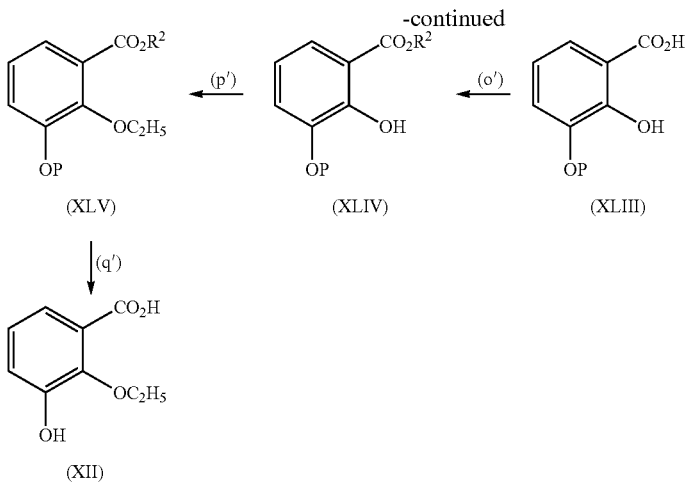

The compound of formula XII where $R^3$ is alkoxy having from 1 to 2 carbon atoms, i.e. compounds of formula:

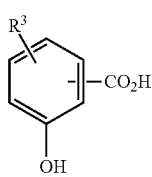

(XII)

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24, 221-8.
JP 07070025.
7. 3-OEt-4-OHC$_6$H$_3$CO$_2$H
WO 9626176.

The compound of formula XII where $R^3$ is alkyl having 1 to 2 carbon atoms, i.e. compounds of formula:

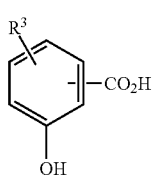

(XII)

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 1. 3-Et-5-OHC$_6$H$_3$CO$_2$H
Adapt synthesis from J.O.C. 2001, 66, 7883-88 by using 2-Ethylacrolein.

Use in Methods of Treatment

This invention provides a method for reducing uric acid levels in a mammalian subject or increasing uric acid excretion from a mammalian subject. The level of uric acid in a mammal can be determined using any conventional measure. Typically the level of uric acid in the blood is determined. Uric acid can also be deposited or precipitated in tissues, resulting in depots (e.g. tophi) that can be affected by raising or lowering blood uric acid concentrations, and which conversely can contribute to circulating uric acid. The method of this invention for reducing uric acid can be used to treat or prevent a variety of conditions including gout, hyperuricemia, elevated levels of uric acid that do not meet the levels customarily justifying a diagnosis of hyperuricemia, kidney stones, renal dysfunction, cardiovascular disease, cardiovascular risk factor, and cognitive impairment. By lowering uric acid levels, administration of the compounds of this invention slows progression of kidney disease. An elevated uric acid level has been identified as a risk factor for cardiovascular disease. A significant correlation has been shown between elevated uric acid and cognitive impairment in older adults. (Schretlen, D. J. et al., "Serum Uric Acid and Cognitive Function in Community-Dwelling Older Adults", Neuropsychology (January 2007) 21(1): 136-140). Accordingly, the method of this invention for reducing uric acid can be used to treat or prevent cognitive impairment, including cognitive impairment in elderly adults. It is well known that people with Lesch-Nyhan Syndrome have elevated levels of uric acid and suffer the numerous consequences of this hyperuricemia, including gout. Thus, this invention for reducing blood levels and increasing elimination of uric acid can be used to treat people with Lesch-Nyhan Syndrome.

The normal range of uric acid in blood is between 3.4 mg/dL and 7.0 mg/dL in men, between 2.4 mg/dL and 6.0 mg/dL in premenopausal women, and from 2.5 mg/dL to 5.5 mg/dL in children. Urate crystal formation/precipitation typically occurs in men at levels of 6.6 mg/dL or higher and in women at levels of 6.0 mg/dL or higher. This illustrates that levels of uric acid that are within the so-called normal range can have undesirable health consequences, even producing gout. Also, what may be in the normal range for the population as a whole may be elevated for the individual. Cardiovascular and other consequences of elevated uric acid can occur with blood levels well within these "normal" ranges. Therefore, a diagnosis of hyperuricemia is not necessarily a prerequisite for the beneficial effects of the compounds of the invention.

This invention includes the treatment of hyperuricemia associated with gout, hypertension, vascular inflammation, heart failure, arterio-venous disorders, myocardial infarct, stroke, pre-eclampsia, eclampsia, sleep apnea, renal dysfunction (including renal failure, end stage renal disease [ESRD]), organ transplant, diuretics, thiazides, cyclosporine, aspirin, vitamin C, nicotinic acid, levodopa (L-DOPA), cytotoxic drugs, and certain antibacterial agents (such as pyrozinamide), cirrhosis, thyroid dysfunction, parathyroid dysfunction, lung cancer, anemia, leukemia, lymphoma, multiple myeloma, tumor-lysis syndrome, thyroid or parathyroid dysfunction, Lesch-Nyhan Syndrome, smoking, alcohol consumption, and psoriasis. This invention includes the treatment of hyperuricemia that can lead to gout, formation of urate crystals, renal dysfunction, graft or organ failure following transplant, endothelial disorders (such as inflammation), chronic heart failure, arterio-venous disorders, pre-eclampsia, eclampsia, hypertension, and cognitive impairment. In embodiments of the method of this invention for treating gout, tissue deposits of uric acid, including but not limited to tophi, are reduced, and the incidence and severity of gout flares are also reduced.

The compounds of this invention can be administered by any conventional route of systemic administration. Preferably they are administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any one of the embodiments of the compounds described above. In the interest of avoiding unnecessary redundancy, each such compound and group of compounds is not being repeated, but they are incorporated into this description of uses and methods of treatment as if they were repeated.

Both human and non-human mammalian subjects can be treated in accordance with the treatment method of this invention. The optimal dose of a particular compound of the invention for a particular subject can be determined in the clinical setting by a skilled clinician. In the case of oral administration the compound of this invention is generally administered to adults in a daily dose of from 1 mg to 2500 mg, more preferably from 1 mg to 1200 mg. In other embodiments of this invention the compound is administered in a dose of from 400 mg to 1000 mg, from 600 mg to 800 mg, from 600 mg to 1000 mg, or from 100 to 300 mg, administered once or twice per day. The average body weight of a typical adult is 60 to 70 kilograms, so that appropriate dose ranges expressed as mg/kg are approximately from 0.015 to 42 mg/kg, from 0.015 to 20 mg/kg, from 6.6 to 13 mg/kg, from 10 to 13 mg/kg, from 10 to 16 mg/kg, or from 1.67 to 4.3 mg/kg, administered once or twice per day. When treating children the optimal dose is determined by the patient's physician. In the case of oral administration to a mouse the compound of this invention is generally administered in a daily dose from 1 to 300 mg of the compound per kilogram of body weight.

The compound of this invention can be administered in combination with other uric acid lowering drugs. In such cases the dose of the compound of this invention is as described above. Any conventional or investigational uric acid lowering drug can be utilized in combination with the compound of this invention. Examples of such drugs include xanthine oxidase inhibitors such as allopurinol (from 100 mg/day to 1000 mg/day; more typically from 100 mg/day to 300 mg/day) febuxostat (from 40 mg/day to 120 mg/day; more specifically from 60 mg/day to 80 mg/day) and oxypurinol; Puricase/PEG-uricase (from 4 mg to 12 mg every two weeks by infusion); uricosuric agents such as sulfinpyrazone (from 100 mg/day to 800 mg/day), probenecid (500 mg/day), losartan (from 25 mg/day to 200 mg/day, more typically from 50 mg/day to 100 mg/day), fenofibrate, JTT-552 (a URAT-1 inhibitor), benzbromarone (from 70 mg/day to 150 mg/day), and statins such as atorvastatin (LIPITOR®). The other uric acid lowering drug can be administered in its usual amount or in an amount that is less than the usual amount, whether by administering lower doses of such other drug or by less frequent dosing with such other drug.

The compounds of this invention can be administered together with other drugs used to decrease the pain associated with gouty attacks, for example nonsteroidal antiinflammatory drugs (NSAIDs), colchicine, corticosteroids, and other analgesics.

In the course of lowering uric acid levels in the blood it is expected that the compounds of this invention will increase the levels of uric acid in the urine. To increase the pH of the urine and thereby improve solubility of the uric acid, citrate or bicarbonate, for example, can be administered in conjunction with the compound of this invention.

An admixture of the compound or salt of this invention with one or more other uric acid lowering drugs, analgesics, and pH increasing agents, can be administered to the subject. Alternatively the compound or salt of this invention and the one or more other uric acid lowering drugs, analgesics, and pH increasing agents are not mixed together to form an admixture but are administered independently to the subject. When the active ingredients are not mixed together to form a single admixture or composition it is convenient to provide them in the form of a kit comprising one or more unit oral doses of a compound of this invention, one or more unit oral doses of one or more other uric acid lowering drugs, analgesics, and pH increasing agents, and instructions for administering the compound of this invention in combination with the other active ingredients. Preferably the components of the kit are packaged together, such as in a box or a blister pack.

Pharmaceutical Compositions

This invention provides a pharmaceutical composition comprising a compound of this invention, and optionally a pharmaceutically acceptable carrier. Further embodiments of the pharmaceutical composition of this invention comprise any one of the embodiments of the compounds described above. In the interest of avoiding unnecessary redundancy, each such compound and group of compounds is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 2500 mg, more preferably from 1 mg to 1200 mg of the compound of this invention. In more specific embodiments of this invention the oral composition will comprise from 400 mg to 1000 mg, from 600 mg to 800 mg, from 600 mg to 1000 mg, or from 100 to 300 mg, of the compound of this invention. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The active ingredients can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

The invention will be better understood by reference to the following examples, which illustrate but do not limit the invention described herein.

EXAMPLES

Example 1

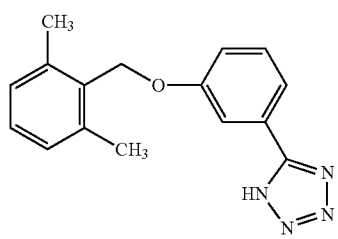 [SMILES: Cc1cccc(C)c1COc1cccc(-c2nnn[nH]2)c1]

5-(3-(2,6-Dimethylbenzyloxy)phenyl)-1H-tetrazole

Step A: Preparation of 3-(2,6-Dimethylbenzyloxy)benzonitrile

A solution of 2,6-Dimethylbenzyl alcohol (6.27 g, 46.1 mmol) and diisopropyl azodicarboxylate (DIAD, 9.24 g, 45.7 mmol) in dry THF (30 ml) was added drop wise to a solution of 3-Hydroxybenzonitrile (5 g, 37 mmol) and triphenylphosphine (TPP, 11.99 g, 45.7 mmol) in THF (100 ml) at 0° C. The reaction mixture was warmed to room temperature for 4 hours or until all the starting material is consumed, diluted with ether and washed with water (2×). The organic layer was dried over $Na_2SO_4$, filtered, concentrated, and purified by flash chromatography on a silica gel column (hex: ethyl acetate 2:1) to give the title compound as a white solid.

Step B: Preparation of 5-(3-(2,6-Dimethylbenzyloxy)phenyl)-1H-tetrazole

A mixture of 3-(2,6-Dimethylbenzyloxy)benzonitrile (Step A, 3 g, 11.8 mmol), sodium azide (0.847 g, 13 mmol) and ammonium chloride (0.697 g, 13 mmol) in dry dimethylformamide (30 ml) was heated under argon at 110° C. for 14 hours or until all the starting material is consumed. Water was added to the reaction mixture to dissolve all the solids; the solution was taken in brine and extracted with ethyl acetate (2×). The combined organic layer was washed with brine, dried over $Na_2SO_4$, filtered, concentrated and purified by flash chromatography on a silica gel column (chloroform: methanol 95:5) to give the title compound as a white solid.

$^1$H NMR (400 MHz, $(CD_3)_2SO$): 2.4 (s, 6H); 5.15 (s, 2H); 7.1 (d, 2H); 7.15 (m, 1H); 7.3 (dd, 1H); 7.5 (t, 1H); 7.65 (m, 1H); 7.7 (m, 1H).

Example 2

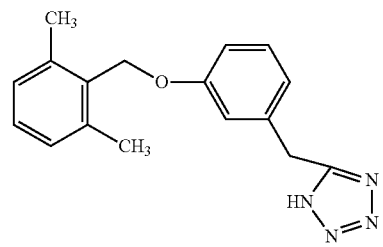 [SMILES: Cc1cccc(C)c1COc1cccc(Cc2nnn[nH]2)c1]

5-(3-(2,6-Dimethylbenzyloxy)benzyl)-1H-tetrazole

Step A: Preparation of 2-(3-Hydroxyphenyl)acetonitrile

To a solution of 2-(3-Methoxyphenyl)acetonitrile (3.6 g, 25.4 mmol) in dry methylene chloride (20 ml) was added $BBr_3$ (55 ml, 1M in $CH_2Cl_2$, 55 mmol) at −78° C. under argon atmosphere. The reaction mixture was warmed to ambient temperature for 48 hours, quenched by crushed ice, and extracted with methylene chloride. The organic layer was dried over $Na_2SO_4$, filtered, concentrated and purified by flash chromatography on a silica gel column ($CH_2Cl_2$: ethyl acetate 4:1) to give the title compound as oil.

Step B: Preparation of 2-(3-(2,6-Dimethylbenzyloxy)phenyl)acetonitrile

A solution of 2-(3-Hydroxyphenyl)acetonitrile (Step A, 5 g, 37 mmol) and diisopropyl azodicarboxylate (DIAD, 3.38 g, 16.7 mmol) in dry THF (20 ml) was added drop wise to a solution of 2,6-Dimethylbenzyl alcohol (2.25 g, 16.5 mmol) and triphenylphosphine (TPP, 4.3 g, 16.4 mmol) in THF (30 ml) at 0° C. under argon. The reaction mixture was stirred at room temperature for 16 hours or until all the starting material is consumed. Silica gel (25 g) was added to the mixture, solvents were removed under reduced pressure, loaded on silica gel column and eluted with methylene chloride:hexane (1:1) to give light yellow crystalline solid.

Step C: Preparation of
5-(3-(2,6-Dimethylbenzyloxy)benzyl)-1H-tetrazole

A mixture of 2-(3-(2,6-Dimethylbenzyloxy)phenyl)acetonitrile (Step B, 3.2 g, 12.7 mmol), sodium azide (1.28 g, 16.7 mmol) and ammonium chloride (1.08 g, 20.2 mmol) in dry dimethylformamide (30 ml) was heated under argon at 90° C. for 9 hours or until all the starting material is consumed and the reaction mixture was concentrated under reduced pressure. The reaction mixture was taken in ethyl acetate and washed with water (2×), dried over $Na_2SO_4$, filtered, concentrated and purified by flash chromatography on a silica gel column (methylene chloride:methanol 9:1) to give the oily product. The oil was stirred with 1:2 ethyl acetate:hexane for 10 minutes, and solid was filtered to give product as a white solid.

$^1$H NMR (400 MHz, $(CD_3)_2SO$): 2.3 (s, 6H); 4.25 (s, 2H); 5.15 (s, 2H); 6.84 (d, 1H); 6.96 (m, 2H); 7.08 (d, 2H); 7.18 (m, 1H); 7.28 (m, 1H).

Example 3

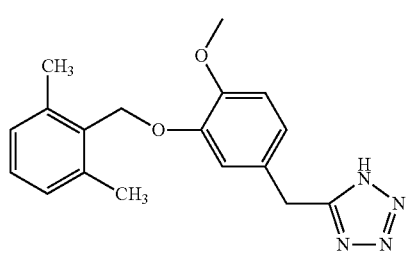 [SMILES: COc1ccc(Cc2nnn[nH]2)cc1OCc1c(C)cccc1C]

5-(3-(2,6-Dimethylbenzyloxy)-4-methoxybenzyl)-1H-tetrazole

Step A: Preparation of Ethyl
3-hydroxy-4-methoxybenzoate

A solution of 3-Hydroxy-4-methoxybenzoic acid (25 g, 148.67 mmol) and p-Toluenesulfonic acid monohydrate (3.17 g, 16.66 mmol) in abs ethanol (300 ml) was refluxed for 6 hours or until all the starting material is consumed. The reaction mixture was concentrated, diluted with EtOAc (60 ml) and washed with water (20 ml). The organic layer was dried over $Na_2SO_4$, filtered, concentrated, and purified by flash chromatography on a silica gel column (hex: ethyl acetate 2:1) to give the title compound.

Step B: Preparation of Ethyl
3-(2,6-dimethylbenzyloxy)-4-methoxybenzoate

A solution of Ethyl 3-hydroxy-4-methoxybenzoate (Step A, 9.10 g, 46.4 mmol) and diisopropyl azodicarboxylate (DIAD, 10.23 g, 50 mmol) in dry THF (20 ml) was added drop wise to a solution of 2,6-Dimethylbenzyl alcohol (6.94 g, 51 mmol) and triphenylphosphine (TPP, 13.27 g, 50 mmol) in dry THF (60 ml) at 0° C. under argon. The reaction mixture was warmed to room temperature for 4 hours or until all the starting material is consumed, diluted with ether and washed with water (2×). The organic layer was dried over $Na_2SO_4$, filtered, concentrated, and purified by flash chromatography on a silica gel column (hex: ethyl acetate 2:1) to give the title compound.

Step C: Preparation of (3-(2,6-dimethylbenzyloxy)-4-methoxyphenyl)methanol

To a solution of Ethyl 3-(2,6-dimethylbenzyloxy)-4-methoxybenzoate (Step B, 6.04 g, 19.23 mmol) in dry THF (30 ml) was added drop wise $LiAlH_4$ (1M in THF, 0.803 g, 21.16 mmol) at 0° C. under argon. The reaction mixture was stirred for 4 hours or until all the starting material is consumed, then quenched slowly with 0.1N HCl, EtOAc (20 ml) was added to the reaction mixture. The reaction mixture was filtered and precipitate was washed with EtOAc (25 ml×2). The combined organic layer was washed with 0.1N HCl, brine, dried over $Na_2SO_4$, filtered, concentrated, and purified by flash chromatography on a silica gel column (hex: ethyl acetate 4:1) to give the title compound.

Step D: Preparation of 2-((5-(bromomethyl)-2-methoxyphenoxy)methyl)-1,3-dimethylbenzene To a solution of (3-(2,6-dimethylbenzyloxy)-4-methoxyphenyl)methanol (Step C, 5.23 g, 20.4 mmol) and $CBr_4$ (10.16 g, 30.6 mmol) in dry $CH_2Cl_2$ (20 ml) was added portion wise triphenylphosphine (8.03 g, 30.64 mmol) at 0° C. The reaction mixture was stirred for 1.5 hours, filtered, concentrated and purified by flash chromatography on a silica gel column (hex: ethyl acetate 2:1) to give the title compound.

$^1$H NMR (400 MHz, $(CDCl_3)$: 2.43 (s, 6H); 3.83 (s, 3H); 4.53 (s, 2H); 5.08 (s, 2H); 6.84 (d, 1H); 7.0-7.03 (dd, 1H); 7.06-7.09 (m, 3H); 7.14-7.18 (m, 1H).

Step E: Preparation of 2-(3-(2,6-Dimethylbenzyloxy)-4-methoxyphenyl)acetonitrile The solution of 2-((5-(bromomethyl)-2-methoxyphenoxy)methyl)-1,3-dimethylbenzene (Step D, 3.28 g, 9.7 mmol) and NaCN (0.624 g, 12.7 mmol) in dry DMF (20 ml) was heated at 120° C. for 2.5 hours then cooled and diluted with EtOAc (50 ml). The organic layer was washed with water (30 ml), brine, dried over $Na_2SO_4$, filtered, concentrated, and purified by flash chromatography on a silica gel column (hex: ethyl acetate 2:1) to give the title compound.

Step F: Preparation of 5-(3-(2,6-Dimethylbenzyloxy)-4-methoxybenzyl)-1H-tetrazole A mixture of 2-(3-(2,6-Dimethylbenzyloxy)-4-methoxyphenyl)acetonitrile (Step E, 2.17 g, 7.5 mmol), sodium azide (0.590 g, 9.1 mmol) and ammonium chloride (0.486 g, 9.1 mmol) in dry DMF (20 ml) was heated under argon at 90° C. for 16 hours or until all the starting material is consumed, the reaction mixture was cooled, diluted with water and extracted with EtOAc (30 ml×4). The combined organic layer was washed with brine, dried over $Na_2SO_4$, filtered, concentrated and purified by flash chromatography on a silica gel column (chloroform:methanol 95:5) to give semi solid product. The semi solid was stirred with 1:2 ethyl acetate:hexane (15 ml) for 10 minutes, and filtered to give product as a white solid.

$^1$H NMR (400 MHz, (CD$_3$)$_2$SO): 2.3 (s, 6H); 3.68 (s, 3H); 4.22 (s, 2H); 4.98 (s, 2H); 6.78-6.81 (dd, 1H); 6.91-6.93 (d, 1H); 7.05-7.07 (d, 2H); 7.13-7.16 (m, 2H). MS: m/z 325.2 [M+H]$^+$.

Example 4

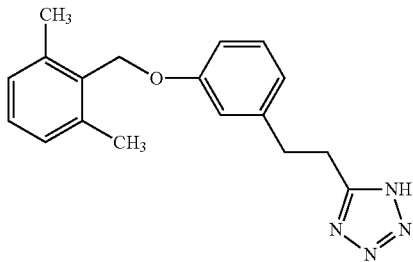 [SMILES: Cc1cccc(C)c1COc1cccc(CCc2nnn[nH]2)c1]

5-(3-(2,6-Dimethylbenzyloxy)phenethyl)-1H-tetrazole

Step A: Preparation of 3-(3-methoxyphenyl)propanenitrile

The solution of 1-(2-bromoethyl)-3-methoxybenzene (10 g, 46.4 mmol), NaCN (2.73 g, 55.8 mmol) in dry DMF (20 ml) was heated at 90° C. for 6 hours or until all the starting material is consumed, the reaction was cooled, diluted with EtOAc (60 ml) and washed with water (20 ml×3), brine, the organic layer was dried over Na$_2$SO$_4$, filtered, concentrated, and purified by flash chromatography on a silica gel column (hex: ethyl acetate 2:1) to give the title compound as an oil.

Step B: Preparation of 3-(3-hydroxyphenyl)propanenitrile

To a stirred solution of 3-(3-methoxyphenyl)propanenitrile (Step A, 1.71 g, 10.6 mmol) in dry CH$_2$Cl$_2$ (20 ml) was added BBr$_3$ (1M in CH$_2$Cl$_2$, 5.32 g, 21.2 mmol) at −78° C. under argon. The reaction mixture was stirred at the same temperature for 2 hours and then at 0° C. for 4 hours or until all the starting material is consumed, quenched with ice, extracted with EtOAc (30 ml×3), the combined organic layer was washed carefully with sat NaHCO$_3$, brine and dried over Na$_2$SO$_4$, filtered, concentrated, and purified by flash chromatography on a silica gel column (hex: ethyl acetate 2:1) to give the title compound.

Step C: Preparation of 3-(3-(2,6-dimethylbenzyloxy)phenyl)propanenitrile

A solution of 3-(3-hydroxyphenyl)propanenitrile (Step B, 1.25 g, 8.5 mmol) and diisopropyl azodicarboxylate (DIAD, 1.87 g, 9.26 mmol) in dry THF (10 ml) was added drop wise to a solution of 2,6-Dimethylbenzyl alcohol (1.27 g, 9.3 mmol) and triphenylphosphine (TPP, 2.43 g, 9.26 mmol) in dry THF (30 ml) at 0° C. under argon. The reaction mixture was warmed to room temperature for 4 hours or until all the starting material is consumed, diluted with ether and washed with water (2×). The organic layer was dried over Na$_2$SO$_4$, filtered, concentrated, and purified by flash chromatography on a silica gel column (hex: ethyl acetate 2:1) to give the title compound.

Step D: Preparation of 5-(3-(2,6-Dimethylbenzyloxy)phenethyl)-1H-tetrazole

A mixture of 3-(3-(2,6-dimethylbenzyloxy)phenyl)propanenitrile (Step C, 2.62 g, 9.9 mmol), sodium azide (0.899 g, 13.8 mmol) and ammonium chloride (0.740 g, 13.8 mmol) in dry DMF (20 ml) was heated under argon at 90° C. for 16 hours or until all the starting material is consumed, the reaction mixture was cooled, diluted with water and extracted with EtOAc (30 ml×4). The combined organic layer was washed with brine, dried over Na$_2$SO$_4$, filtered, concentrated and purified by flash chromatography on a silica gel column (chloroform:methanol 95:5→92.5:7.5) to give semi solid product. The semi solid was stirred with 1:2 ethyl acetate:hexane (15 ml) for 10 minutes, and filtered to give product as a white solid.

$^1$H NMR (400 MHz, (CD$_3$)$_2$SO): 2.48 (s, 6H); 3.02 (t, 2H); 3.19 (t, 2H); 4.98 (s, 2H); 6.80-6.81 (d, 1H); 6.86-6.89 (m, 2H); 7.05-7.07 (d, 2H); 7.14-7.23 (m, 2H). MS: m/z 309.2 [M+H]$^+$.

Example 5

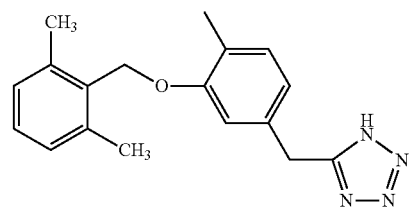 [SMILES: Cc1ccc(Cc2nnn[nH]2)cc1OCc1c(C)cccc1C]

5-(3-(2,6-Dimethylbenzyloxy)-4-methylbenzyl)-1H-tetrazole

Step A: Preparation of 2-(3-Hydroxy-4-methylphenyl)acetonitrile

To a stirred solution of 2-(3-methoxy-4-methylphenyl)acetonitrile (5 g, 31 mmol) in dry CH$_2$Cl$_2$ (20 ml) was added drop wise BBr$_3$ (1M in CH$_2$Cl$_2$, 10.02 g, 40 mmol) at −78° C. under argon. The reaction mixture was stirred at the same temperature for 2 hours and then at 0° C. for 5 hours or until all the starting material is consumed, quenched with ice, extracted with EtOAc (30 ml×3), the combined organic layer was washed carefully with sat NaHCO$_3$, brine and dried over Na$_2$SO$_4$, filtered, concentrated, and purified by flash chromatography on a silica gel column (hex: ethyl acetate 4:1→CH$_2$Cl$_2$: hex 1:1) to give the title compound as an off white solid.

Step B: Preparation of 2-(3-(2,6-dimethylbenzyloxy)-4-methylphenyl)acetonitrile

To a stirred solution of 2-(3-Hydroxy-4-methylphenyl)acetonitrile (Step A, 2.18 g, 14.8 mmol), K$_2$CO$_3$ (2.66 g, 19.2 mmol) in dry DMF (20 ml) was added 2,6-Dimethylbenzyl chloride (2.97 g, 19.2 mmol) at room temperature under argon. The reaction mixture was stirred for 16 hours, diluted with EtOAc (40 ml), washed with water (20 ml) and brine. The organic layer was dried over Na$_2$SO$_4$, filtered, concentrated, and purified by flash chromatography on a silica gel column (hex: ethyl acetate 2:1) to give the title compound as a white solid.

Step C: Preparation of 5-(3-(2,6-Dimethylbenzyloxy)-4-methylbenzyl)-1H-tetrazole A mixture of 2-(3-(2,6-dimethylbenzyloxy)-4-methylphenyl)acetonitrile (Step B, 1.12 g, 4.2 mmol), sodium azide (0.400 g, 6.1 mmol) and ammonium chloride (0.350 g, 6.5 mmol) in dry DMF (15 ml) was heated under argon at 90° C. for 16 hours or until all the starting material is consumed, the reaction mixture was cooled, diluted with water and extracted with EtOAc (30 ml×4). The combined organic layer was washed with brine, dried over $Na_2SO_4$, filtered, concentrated and purified by flash chromatography on a silica gel column (chloroform:methanol 95:5→92.5:7.5) to give semi solid product. The semi solid was stirred with 1:2 ethyl acetate: hexane (15 ml) for 10 minutes, and filtered to give product as a white solid.

$^1$H NMR (400 MHz, $(CD_3)_2SO$): 2.0 (s, 3H); 2.35 (s, 6H); 4.27 (s, 2H); 5.0 (s, 2H); 6.73-6.75 (dd, 1H); 7.08-7.1 (m, 3H); 7.15-7.19 (m, 2H). MS: m/z 309.2 $[M+H]^+$.

Example 6

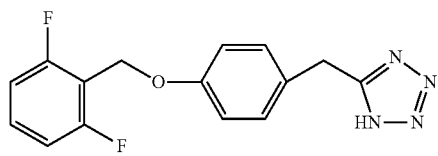 [SMILES: Fc1cccc(F)c1COc1ccc(Cc2nnn[nH]2)cc1]

5-(4-(2,6-Difluorobenzyloxy)benzyl)-1H-tetrazole

Step A: Preparation of 2-(4-(2,6-Difluorobenzyloxy)phenyl)acetonitrile

To a solution of 2-(4-Hydroxyphenyl)acetonitrile (5 g, 37.5 mmol) and $K_2CO_3$ (6.74 g, 48.8 mmol) in dry DMF (20 ml) was added 2,6-Difluorobenzyl bromide (7.77 g, 37.5 mmol). The reaction mixture was stirred for 4 hours at room temperature and concentrated in vacuo. The crude residue was taken in EtOAc and washed with water and brine. The aqueous layer was washed one more time with EtOAc. The combined organic layer was dried over $Na_2SO_4$, filtered, and concentrated to provide the title compound as a white solid.

$^1$H NMR (270 MHz, $CDCl_3$): 3.65 (s, 2H); 5.1 (s, 2H); 6.9-7.0 (m, 4H); 7.2-7.4 (m, 3H).

Step B: Preparation of 5-(4-(2,6-Difluorobenzyloxy)benzyl)-1H-tetrazole

A mixture of 2-(4-(2,6-Difluorobenzyloxy)phenyl)acetonitrile (Step A, 5 g, 19.3 mmol), sodium azide (1.3 g, 20 mmol), and ammonium chloride (1.06 g, 20 mmol) in dry DMF (60 ml) was heated at 90° C. for 16 hours. The solvent was removed in vacuo and the oily residue was partitioned between EtOAc and water (acidified to pH 1 with conc. HCl). The organic layer was washed with water, dried over $Na_2SO_4$, filtered and concentrated to a brown semisolid. The purification was done by flash chromatography on silica gel column (chloroform:methanol, 9:1) to provide the title compound as a light creamy solid.

$^1$H NMR (270 MHz, $CDCl_3$): 4.0 (s, 2H); 5.1 (s, 2H); 6.7-6.9 (m, 4H); 7.0 (d, 2H); 7.2 (m, 1H).

Example 7

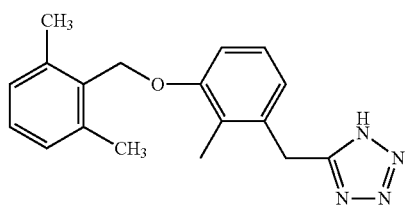 [SMILES: Cc1cccc(C)c1COc1cccc(Cc2nnn[nH]2)c1C]

5-(3-(2,6-Dimethylbenzyloxy)-2-methylbenzyl)-1H-tetrazole

Step A: Preparation of Ethyl 3-hydroxy-2-methylbenzoate

A solution of 3-Hydroxy-2-methylbenzoic acid (5.04 g, 33.12 mmol) and p-Toluenesulfonic acid monohydrate (0.741 g, 3.89 mmol) in abs ethanol (150 ml) was refluxed for 16 hours or until all the starting material is consumed. The reaction mixture was concentrated, diluted with EtOAc (30 ml) and washed with water (20 ml). The organic layer was dried over $Na_2SO_4$, filtered, concentrated, and purified by flash chromatography on a silica gel column (hex: ethyl acetate 2:1) to give the title compound.

Step B: Preparation of Ethyl 3-(2,6-dimethylbenzyloxy)-2-methylbenzoate

To a stirred solution of Ethyl 3-hydroxy-2-methylbenzoate (Step A, 3.1 g, 17.22 mmol), $K_2CO_3$ (3.09 g, 22.38 mmol) in dry DMF (15 ml) was added 2,6-Dimethylbenzyl chloride (3.19 g, 20.66 mmol) at room temperature under argon. The reaction mixture was stirred for 16 hours, diluted with EtOAc (40 ml), washed with water (20 ml) and brine. The organic layer was dried over $Na_2SO_4$, filtered, concentrated, and purified by flash chromatography on a silica gel column (hex: ethyl acetate 4:1) to give the title compound as a white solid.

Step C: Preparation of (3-(2,6-dimethylbenzyloxy)-2-methylphenyl)methanol

To a solution of Ethyl 3-(2,6-dimethylbenzyloxy)-2-methylbenzoate (Step B, 5.94 g, 19.93 mmol) in dry THF (35 ml) was added drop wise $LiAlH_4$ (1M in THF, 0.832 g, 21.92 mmol) at 0° C. under argon. The reaction mixture was stirred for 4 hours or until all the starting material is consumed, then quenched slowly with 0.1N HCl at 0° C., and EtOAc (20 ml) was added to the reaction mixture. The reaction mixture was filtered and precipitate was washed with EtOAc (25 ml×2). The combined organic layer was washed with 0.1N HCl, brine, dried over $Na_2SO_4$, filtered, concentrated, and purified by flash chromatography on a silica gel column (hex: ethyl acetate 2:1) to give the title compound.

Step D: Preparation of 1-(bromomethyl)-3-(2,6-dimethylbenzyloxy)-2-methylbenzene To a solution of (3-(2,6-dimethylbenzyloxy)-2-methylphenyl)methanol (Step C, 3.68 g, 14.37 mmol) and $CBr_4$ (5.25 g, 15.8 mmol) in dry CH$_2$Cl$_2$ (20 ml) was added portion wise triphenylphosphine (4.14 g, 15.8 mmol) at 0° C. The reaction mixture was stirred for 4 hours, filtered, concentrated and purified by flash chromatography on a silica gel column (hex: ethyl acetate 4:1) to give the title compound. The solid was further kept under vacuum for 6 hours to dry.

Step E: Preparation of 2-(3-(2,6-Dimethylbenzyloxy)-2-methylphenyl)acetonitrile

The solution of 1-(bromomethyl)-3-(2,6-dimethylbenzyloxy)-2-methylbenzene (Step D, 4.28 g, 13.41 mmol) and NaCN (0.789 g, 16.10 mmol) in dry DMF (20 ml) was heated at 120° C. for 3 hours then cooled and diluted with EtOAc (50 ml). The organic layer was washed with water (30 ml), brine, dried over Na$_2$SO$_4$, filtered, concentrated, and purified by flash chromatography on a silica gel column (hex: ethyl acetate 4:1) to give the title compound.

Step F: Preparation of 5-(3-(2,6-Dimethylbenzyloxy)-2-methylbenzyl)-1H-tetrazole A mixture of 2-(3-(2,6-Dimethylbenzyloxy)-2-methylphenyl)acetonitrile (Step E, 2.70 g, 10.19 mmol), sodium azide (0.795 g, 12.23 mmol) and ammonium chloride (0.653 g, 12.22 mmol) in dry DMF (20 ml) was heated under argon at 90° C. for 16 hours or until all the starting material is consumed, the reaction mixture was cooled, diluted with water and extracted with EtOAc (30 ml×4). The combined organic layer was washed with brine, dried over Na$_2$SO$_4$, filtered, concentrated and purified by flash chromatography on a silica gel column (chloroform:methanol 92.5:7.5) to give semi solid product. The semi solid was stirred with 1:2 ethyl acetate:hexane (15 ml) for 10 minutes, and filtered to give product as a white solid.
$^1$H NMR (400 MHz, (CD$_3$)$_2$SO): 2.01 (s, 3H); 2.32 (s, 6H); 4.24 (s, 2H); 5.01 (s, 2H); 6.78-6.79 (dd, 1H); 7.06-7.08 (d, 2H); 7.12-7.19 (m, 3H).

Example 8

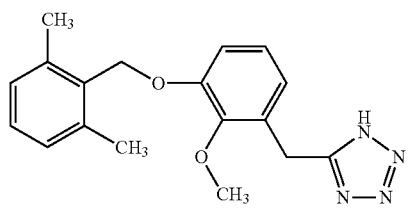 [SMILES: COc1c(Cc2nnn[nH]2)cccc1OCc1c(C)cccc1C]

5-(3-(2,6-Dimethylbenzyloxy)-2-methoxybenzyl)-1H-tetrazole

Step A: Preparation of 3-(2,6-Dimethylbenzyloxy)-2-methoxybenzaldehyde

The solution of 3-hydroxy-2-methoxybenzaldehyde (5.06 g, 32.7 mmol), 2,6-Dimethylbenzyl chloride (5.04 g, 33.1 mmol) and K$_2$CO$_3$ (4.78 g, 34.6 mmol) in dry DMF (15 ml) was stirred at room temperature under argon for 16 hours, then diluted with EtOAc (40 ml), and washed with water (20 ml). The organic layer was concentrated, and purified by flash chromatography on a silica gel column (hex: ethyl acetate 4:1) to give the title compound as an off white solid.

Step B: Preparation of (3-(2,6-dimethylbenzyloxy)-2-methoxyphenyl)methanol

To a solution of 3-(2,6-Dimethylbenzyloxy)-2-methoxybenzaldehyde (Step B, 10.6 g, 32.7 mmol) in dry THF (40 ml) was added drop wise LiAlH$_4$ (1M in THF, 0.95 g, 23.7 mmol) at 0° C. under argon. The reaction mixture was stirred for 1 hours or until all the starting material is consumed, then quenched by adding water slowly, followed by addition of 1N HCl (5 ml), water (10 ml), and EtOAc (20 ml) was added to the reaction mixture. The reaction mixture was concentrated, and passed through a short silica gel column using ethyl acetate to give the title compound as an off white solid.

Step C: Preparation of 3-(2,6-dimethylbenzyloxy)-2-methoxybenzyl methanesulfonate To a solution of (3-(2,6-dimethylbenzyloxy)-2-methoxyphenyl)methanol (Step B, 9.5 g, 32.7 mmol) and triethylamine (5.80 g, 57.4 mmol) in dry CH$_2$Cl$_2$ (100 ml) was added drop wise methanesulfonyl chloride (3.5 ml, 45 mmol) at 0° C. under argon. The reaction mixture was warmed to room temperature for 6 hours or until all the starting material is consumed, neutralized with cooled 10% Na$_2$CO$_3$ and extracted with CH$_2$Cl$_2$. The organic layer was concentrated, and purified by flash chromatography on a silica gel column (hex: methylene chloride 2:1) to give the title compound as light yellow oil Step D: Preparation of 2-(3-(2,6-dimethylbenzyloxy)-2-methoxyphenyl)acetonitrile The solution of 3-(2,6-dimethylbenzyloxy)-2-methoxybenzyl methanesulfonate (Step C, 8.8 g, 30.26 mmol) and NaCN (1.60 g, 32.6 mmol) in dry DMF (40 ml) was heated at 85° C. for 18 hours then cooled and diluted with EtOAc (50 ml). The organic layer was washed with water (30 ml), concentrated, and passed through short silica gel column using methylene chloride to give the title compound as a yellow solid.

Step E: Preparation of 5-(3-(2,6-Dimethylbenzyloxy)-2-methoxybenzyl)-1H-tetrazole A mixture of 2-(3-(2,6-dimethylbenzyloxy)-2-methoxyphenyl)acetonitrile (Step D, 3.2 g, 12.7 mmol), sodium azide (0.86 g, 13.2 mmol) and ammonium chloride (0.696 g, 13.0 mmol) in dry DMF (10 ml) was heated under argon at 90° C. for 16 hours or until all the starting material is consumed, the reaction mixture was cooled, and concentrated under reduced pressure and purified by flash chromatography on a silica gel column (chloroform:methanol 9:1) to give semi solid product. The semi solid was stirred with 1:2 ethyl acetate:hexane (15 ml) for 10 minutes, and filtered to give product as a white solid.
$^1$H NMR (400 MHz, (CD$_3$)$_2$SO): 2.33 (s, 6H); 3.5 (s, 3H); 4.21 (s, 2H); 5.04 (s, 2H); 6.83-6.85 (dd, 1H); 7.05-7.09 (m, 3H); 7.15-7.23 (m, 2H).

Example 9

URAT1 Inhibition Assay

URAT1 (Uric Acid Transporter 1) is expressed on the apical membrane in renal tubules. It mediates the re-uptake of uric acid from the urine into the blood. Inhibition of URAT1 leads to increased excretion of uric acid in the urine, and is therefore a potential mode of action for drugs that lower serum uric acid concentrations. Probenecid and Benzbromarone, for example, have been used clinically for treatment of gout and hyperuricemia, and they both act on URAT1 to reduce uric acid reuptake. However, benzbromarone was withdrawn from the market due to liver toxicity via mechanisms independent of URAT1, and probenecid acts on numerous transporter proteins, resulting in interactions with a variety of other drugs.

An in vitro URAT1 assay is useful for identifying compounds with potential activity in lowering serum uric acid. A suitable assay involves transfection of cells (e g human embryonic kidney cells; "HEK") with a vector encoding human URAT1, followed by determination of the ability of transfected cells to take up radiolabeled uric acid. The activity of compounds as URAT1 inhibitors is evaluated by their ability to block uric acid uptake by transfected cells.

Test Compounds and Chemicals:

Benzbromarone (Sigma, Cat. No. B5774), Probenecid (Sigma, Cat. No. P8761)), DMSO (Sigma, Cat. No. D-2650), [8-$^{14}$C] Urate (50-60 mCi/mmol; American Radio Chemicals, Cat. No. ARC0513).

Subcloning of hURAT1 into the Expression Vector:

Plasmid vector pCMV6-XL5 containing hURAT1 cDNA (Cat. No. SC125624) and the expression vector pCMV6-Neo (Cat. No. pCMVNEO) were obtained from OriGene Technologies, Inc. The full-length hURAT1 cDNA was obtained from the vector pCMV6-XL5 and subcloned into the expression vector pCMV6-Neo to create the hURAT1 expression plasmid pCMV6-hURAT1. The sequences were verified by automatic DNA sequencing.

Cell Culture, Transfection of URAT1 Expressing Plasmids and the Establishment of Stably Expressing HEK Cells for hURAT1:

Human embryonic kidney 293 (HEK) cells (ATTCC, Cat No. CRL-1573) were cultured in EMEM supplemented with 10% FBS and 2 mM L-glutamine and incubated at 37° C. and 5% $CO_2$. For transfection experiments, cells were plated on 60 mm dishes in 1 ml media per dish. After an 18-24 hour incubation, cells were transfected with plasmid pCMV6-hURAT1 or the expression vector pCMV6-Neo, using the Lipofectin transfection agent following the manufacturer's instructions (Invitrogen, Cat. No. 18292). After transfection cells were grown in EMEM media for 72 hours and then by adding 1 mg/ml Geneticin (GIBCO, Cat. No 10131) stable transfectants were selected. Stable transfectants expressing hURAT1 (herein after referred as hURAT1-HEK cells) or cells having only the expression vector pCMV6-Neo (herein after referred as mock-HEK cells) were verified using reverse transcription polymerase chain reaction (RT-PCR) methods.

[8-$^{14}$C] Urate Uptake Assay:

hURAT1-HEK cells and mock-HEK cells were plated in poly-D-Lysine Cell culture 24 well plates (Becton Dickinson, Cat. No. 354414) at a concentration of $3 \times 10^5$ in EMEM medium and incubated overnight. Reaction solutions containing the [8-$^{14}$C] urate (55 mCi/mmol) at a final concentration of 50 μM were prepared with or without test compounds in Hanks' balanced salt solution (HBSS) containing 125 mM sodium gluconate, 4.8 mM potassium gluconate, 1.3 mM calcium, 5.6 mM glucose, 1.2 mM magnesium sulfate, 1.2 mM $KH_2PO_4$ and 25 mM HEPES (pH7.4). Before the uptake assay started, the culture medium was removed and the cells were incubated for 5 min in 0.6 ml of HBSS. After that HBSS was removed, the prepared reaction solutions were added into each well and incubated for 5 min at room temperature. Then the reaction solution was removed, cells were washed twice with 0.6 ml of cold HBSS and lysed with 0.2 ml of 0.1 M NaOH for 20 min. The cell lysates were transferred into the scintillation vials containing 1 ml of scintillation fluid (Opti Phase SuperMIX, PerkinElmer, Cat No. 1200-439) and the radioactivity was counted in the Microbeta counter (1450, Wallac Jet, PerkinElmer). Test compounds were dissolved in DMSO and the same concentration of DMSO was added into the wells of mock-HEK cells and the hURAT1-HEK cells that didn't contain test compounds. For each test compound, the uptake assay was performed 2 times and carried out in triplicate. Urate uptake of the cells for each test condition was presented as the average percent inhibition in comparison to the DMSO control. The radioactivity values obtained for the wells that contained DMSO were taken as 100% uptake of the cells. The observed concentration-percent inhibition data were fitted to a sigmoidal concentration-effect model, where:

$$\% \text{ Inhibition} = (100 \ast \text{Conc}^\wedge\text{Slope})/(\text{IC50}^\wedge\text{Slope} + \text{Conc}^\wedge\text{Slope})$$

$IC_{50}$ and slope estimates with their 95% confidence limits were determined by a non-linear, least-squares regression analysis using the Data Analysis Toolbox™ (MDL Information Systems, San Leandro, Calif., USA).

For assessment of activity of compounds as URAT1 inhibitors, the percent inhibition of uric acid uptake was typically assessed at a drug concentration of 10 micromolar (Table1). Additional drug concentrations of some compounds were tested for determination of IC-50 values (Table 2). In this example the compounds were not necessarily tested simultaneously.

TABLE 1

Inhibitory effects of the test compounds at the concentration of 10 μM on $^{14}$C urate uptake in hURAT1-HEK cells

| Test Compound | % of Inhibition | S.D. |
|---|---|---|
| EB | 90.0 | 0.29 |
| EC | 95.2 | 0.67 |
| ED | 96 | 0.7 |
| EF | 92 | 0.6 |
| EG | 95.57 | 0.39 |
| BD | 56.57 | 2.64 |
| EH | 80.00 | 1.29 |
| EI | 44.00 | 1.53 |

TABLE 2

| Compound | IC50 values (μM) |
|---|---|
| EB | 0.93 |
| EC | 0.24 |
| ED | 0.25 |
| EF | 0.74 |
| EG | 0.13 |
| Benzbromarone | 0.75 |
| Probenecid | 174 |

Example 10

Mouse Oral Single-Dose Pharmacokinetic Study with Compound EB

Determination of the Plasma profile of Compound EB following single oral gavage administration to male mice:

Test compounds were suspended in 1% HPMC using a tissue homogenizer to minimize particles and maximize uniformity of the suspension and stored at 4° C. The formulations was thoroughly mixed just prior to administration. A dose of 100 mg/kg of Compound EB or vehicle (1% HPMC) was administered to male mice by single oral gavage. Mice were placed in urine collectors after dosing for 5 hours, and the total urine output for 5 hours was collected. Samples were frozen at −80° C. until analyzed using LC/MS-MS.

At 0, 0.5, 1, 2, 4, 6, 8 and 24 hours post-dose time points, blood samples (0.4 mL) were collected by orbital sinus bleeds in $K_3$EDTA tubes. The blood samples were centrifuged within 30 minutes of collection under refrigeration (2-8° C.) for 7 minutes at 6000 rpm. Following centrifugation, the plasma were harvested into a single tube for each animal at each time point and immediately frozen at −80° C. until analyzed using LC/MS-MS. Data was subjected to pharmacokinetic analyses using WinNonlin Standard (v2.1, Pharsight Corporation) and Microsoft EXCEL.

Protocol:

A. Plasma.

1. Mice received single oral gavage of Compound EB, 100 mg/kg, and plasma was collected at certain times.
2. Plasma was stored at −80° C. until the day of analysis.
3. Samples were thawed on 37° C. bath for 5 min and vortexed at top speed for 10 sec.
4. Mouse plasma, 0.1 mL was mixed with 0.2 mL Acetonitrile, vortexed 1 min, spun down 14000 rpm, 17000 g, at 4° C., for 25 min.
5. Supernatants were filtered through 0.45 micron, 4 mm, PTFE membrane syringe filter (Phenomenex # AF0-3102-52), and 13 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 100 bar, 37° C. column temperature, method 406975M1, Sequence 1029-08A, Agilent 1100 LC-MS.

All samples were run in duplicate, 210 nm and 230 nm Absorbances, Negative and Positive ionization spectrograms recorded.

B. Calibration Curve.

Step 1. Plasma from "Vehicle" animals (pooled), 0.095 mL, was mixed with 0.005 mL 20× stock of Compound EB in Methanol to make 500 microM, 250 microM, 125 microM, . . . , concentrations of Compound EB in plasma.

For example: 95 microL plasma+5 microL of 10 mM Compound EB in methanol=0.1 mL plasma with 500 microM Compound EB.

Step 2. Samples from step 1 were vortexed for 10 sec at top speed.

Step 3. 0.2 mL of acetonitrile was added to all samples from Step 2, and all vials were vortexed at top speed for 1 min.

Step 4. All samples from step 3 were spun down 14000 rpm, 17000 g, at 4° C., for 25 min.

Step 5. Supernatants were filtered through 0.45 micron, 4 mm, PTFE membrane syringe filter (Phenomenex # AF0-3102-52), 13 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 ml/min, 100 bar, 37° C. column temp, method 406975M1, Agilent 1100 LC-MS.

All samples were run in duplicate, 210 nm and 230 nm Absorbances, Negative and Positive ionization spectrograms recorded.

HPLC conditions:

TABLE 3

HPLC gradient

| Time, Min | Solvent C % | Solvent D % |
|---|---|---|
| 0 | 60 | 40 |
| 2 | 60 | 40 |
| 52 | 31 | 69 |
| 58 | 31 | 69 |
| 60 | 60 | 40 |
| 75 | 60 | 40 |

Solvent C: 0.1% Formic Acid in water
Solvent D: 0.1% Formic Acid, 89.9% Acetonitrile, 10% Methanol Results:

Compound EB was readily detected in mouse plasma, Retention times and mass confirmed in Positive and Negative ionization modes. AGILENT LC-MS sequence 1029-08A.
"M−"=279.2 100%,
"M+"=281.2 100%
Formula weight 280, Retention Time average=26.5 min

TABLE 4

Compound EB concentration in plasma, individual animals

| Mouse plasma Sample # | Bleed Time, HR | Compound EB concentr. μg/mL |
|---|---|---|
| 1 | 0 | 0 |
| 2 | 0 | 0 |
| 3 | 0 | 0 |
| 6 | 0.5 | 206.5 |
| 7 | 0.5 | 207.5 |
| 8 | 0.5 | 134.2 |
| 9 | 1 | 210 |
| 10 | 1 | 139.7 |
| 11 | 1 | 157.6 |
| 12 | 2 | 139.9 |
| 13 | 2 | 187.6 |
| 14 | 2 | 82.4 |
| 15 | 4 | 74.9 |
| 16 | 4 | 92.1 |
| 17 | 4 | 39.6 |
| 18 | 6 | 58.7 |
| 19 | 6 | 79.9 |
| 20 | 6 | 48 |
| 21 | 8 | 18.2 |
| 22 | 8 | 10.7 |
| 23 | 8 | 0 |
| 24 | 24 | 0 |
| 25 | 24 | 0 |
| 26 | 24 | 0 |

TABLE 5

Figure 3:
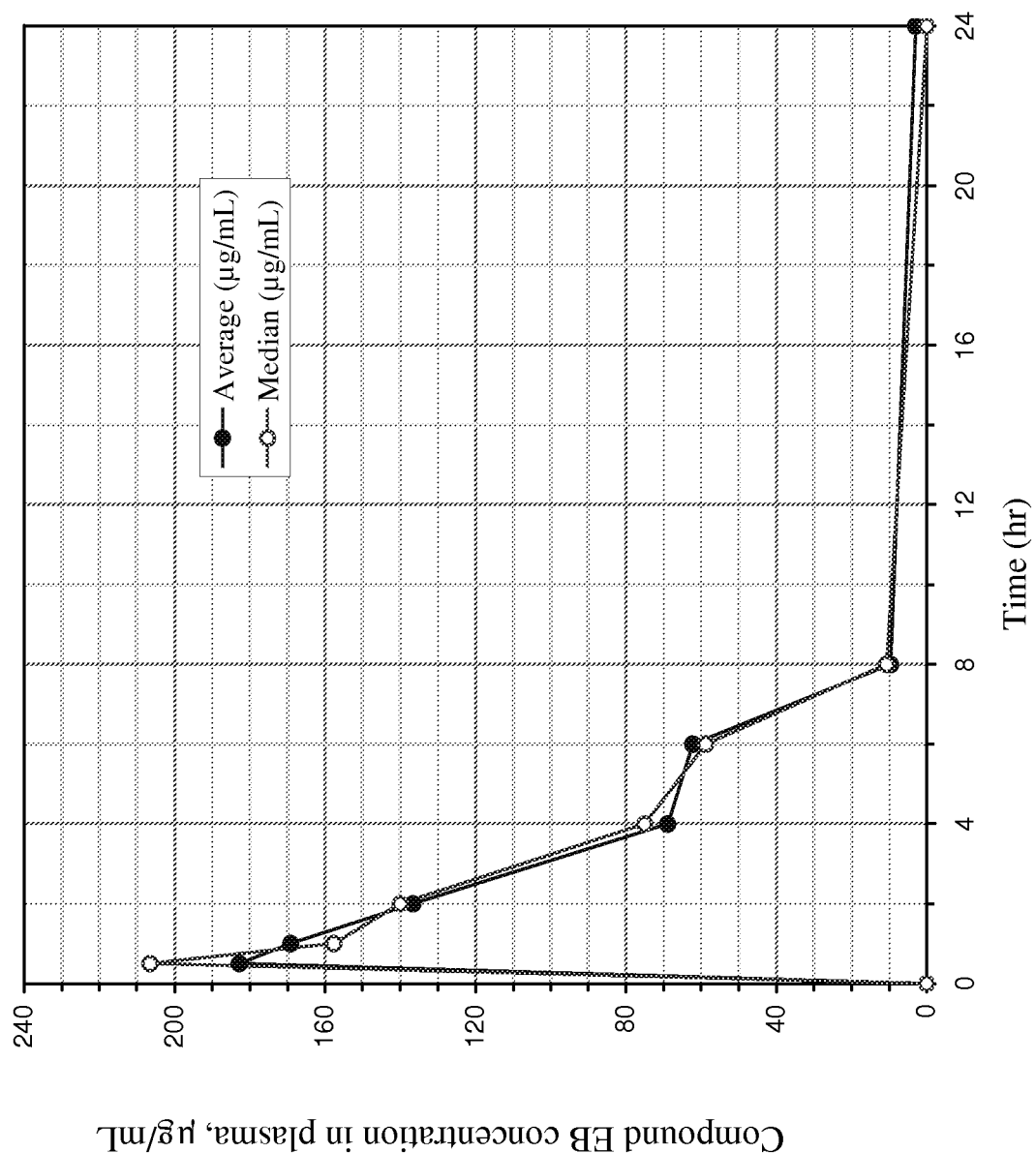
FIG. 3: Compound EB concentration in mouse plasma

Compound EB concentration in plasma, average. (See also FIG. 3).

| Time, hr | Average (μg/mL) |
|---|---|
| 0 | 0 |
| 0.5 | 183 |
| 1 | 169 |
| 2 | 137 |
| 4 | 69 |
| 6 | 62 |
| 8 | 10 |
| 24 | 3 |

$AUC_{0-24}$: 796 μg/mL
Cmax: 210 μg/mL

Linear Components on Semilog Plot:
t1/2 (1-4 hr): 2.27
t1/2 (6-8 hr): 0.74
t1/2 (8-24 hr): 9.39

Example 11

Rat Pilot Single-Dose Oral Pharmacokinetic Study with Compound EB

Determination of the plasma profile of Compound EB following single oral gavage administration to male rats.

Test compound was suspended in 1% HPMC using a tissue homogenizer to minimize particles and maximize uniformity of the suspension and stored at 4° C. The formulations was thoroughly mixed just prior to administration. A dose of 100 mg/kg of test compounds or vehicle (1% HPMC) was administered to male Sprague-Dawley rats by single oral gavage. At 0, 1, 2, 4, 6, 8 and 24 hours post-dose time points, blood samples (0.4 mL) were collected by orbital sinus bleeds in $K_3$EDTA tubes. The blood samples were centrifuged within 30 minutes of collection under refrigeration (2-8° C.) for 7 minutes at 6000 rpm. Following centrifugation, the plasma were harvested into a single tube for each animal at each time point and immediately frozen at −80° C. until analyzed using LC/MS-MS. Serial plasma concentration time data was subjected to pharmacokinetic analyses using WinNonlin Standard (v2.1, Pharsight Corporation) and Microsoft EXCEL.
Protocol:
A. Plasma.
1. Rats received single oral gavage of Compound EB, 100 mg/kg, and plasma was collected at certain times.
2. Plasma was stored at −80° C. until the day of analysis.
3. Samples were thawed on 37° C. bath for 5 min and vortexed at top speed for 10 sec.
4. Rat plasma, 0.1 mL was mixed with 0.2 mL Acetonitrile, vortexed 1 min, spun down 14000 rpm, 17000 g, at 4° C., for 25 min.
5. Supernatants were filtered through 0.45 micron, 4 mm, PTFE membrane syringe filter (Phenomenex # AF0-3102-52), and 13 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 100 bar, 37° C. column temperature, method 406975M1, AGILENT sequence 1015-08A, Agilent 1100 LC-MS.
All samples were run in duplicate, 210 nm and 230 nm Absorbances, Negative and Positive ionization spectrograms were recorded.
B. Calibration Curve.
Step 1. Plasma from "Vehicle" animals (pooled), 0.19 mL, was mixed with 0.01 mL 20× stock of PN2107 in Methanol to make 500 microM, 250 microM, 125 microM, . . . , concentrations of Compound EB in plasma.
For example: 190 microL plasma+10 microL of 10 mM Compound EB in methanol=0.2 mL plasma with 500 microM Compound EB.
Step 2. Samples from step 1 were vortexed for 10 sec at top speed.
Step 3. 0.4 mL of acetonitrile was added to all samples from Step 2, and all vials were vortexed at top speed for 1 min.
Step 4. All samples from step 3 were spun down 14000 rpm, 17000 g, at 4° C., for 25 min.
Step 5. Supernatants were filtered through 0.45 micron, 4 mm, PTFE membrane syringe filter (Phenomenex # AF0-3102-52), 13 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 ml/min, 100 bar, 37° C. column temperature.

All samples were run in duplicate, 210 nm and 230 nm Absorbances, Negative and Positive ionization spectrograms were recorded.

TABLE 6

HPLC conditions
HLPC gradient

| time min | solvent C % | solvent D % |
|---|---|---|
| 0 | 60 | 40 |
| 2 | 60 | 40 |
| 52 | 31 | 69 |
| 58 | 31 | 69 |
| 60 | 60 | 40 |
| 75 | 60 | 40 |

Figure 4:
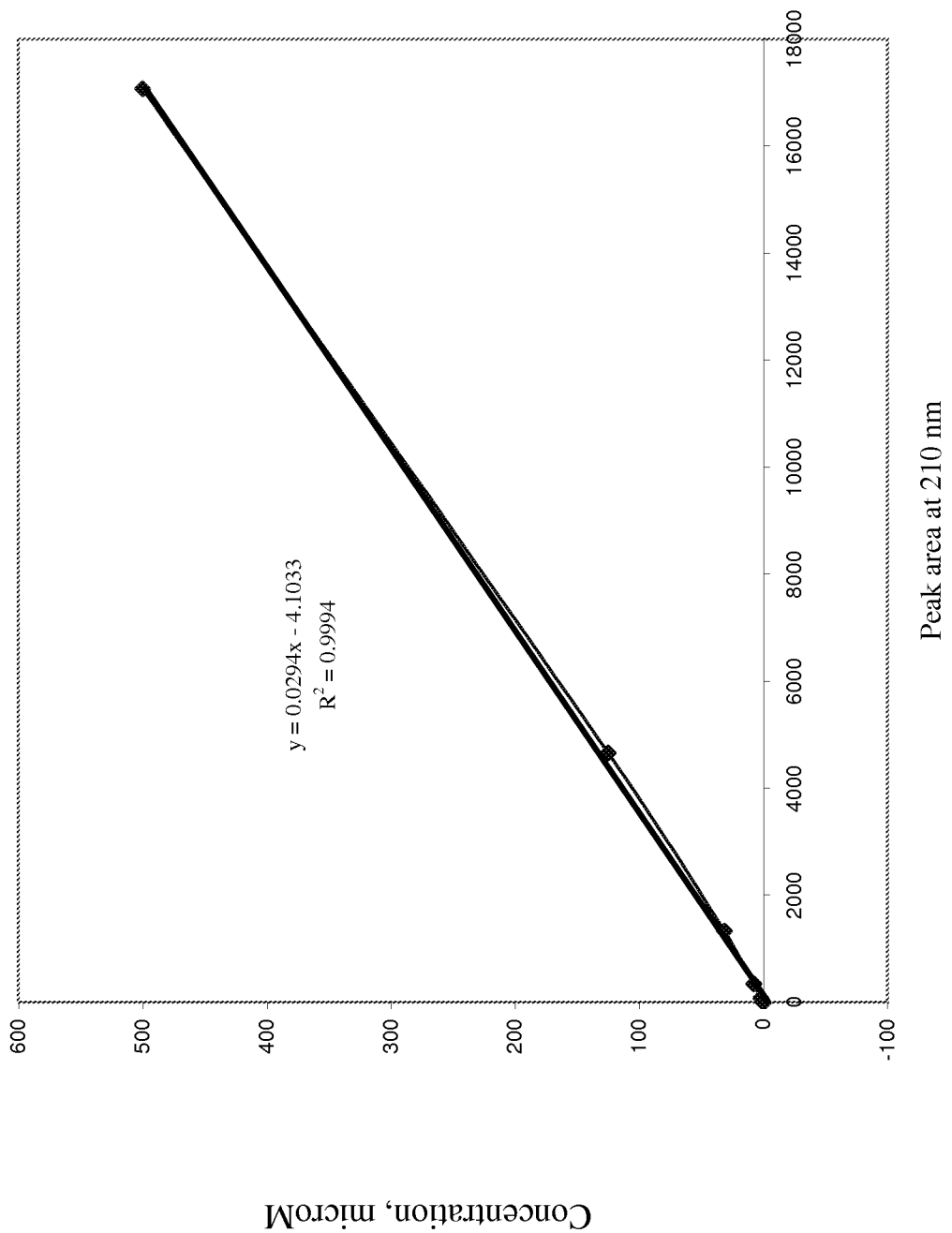
FIG. 4: Compound EB calibration curve in rat plasma, LC-MS

Solvent C: 0.1% Formic Acid in water
Solvent D: 0.1% Formic Acid, 89.9% Acetonitrile, 10% Methanol Results:
1. Calibration curve was built with R^2 fit to linearity=0.9994 (FIG. 4).
2. Compound EB was readily detected in rat plasma, Retention times and mass confirmed in Positive and Negative ionization modes.
"M−"=279.2 100%
"M+"=281.2 100%
Formula weight 280, Retention Time average=26.5 min
Raw data and calculations are listed in Table 7.
Compounds concentrations in plasma are listed in Table 8.

TABLE 7

| | | Compound EB | | | |
|---|---|---|---|---|---|
| | | Peak area at 210 nm | | | in plasma Concentr. |
| Animal ## | Bleed time | run 1 | run 2 | Mean | microM |
| rat 1A | 15 min | 5588 | 5530 | 5559 | 159 |
| rat 1B | 2 HR | 7110 | 7168 | 7139 | 206 |
| rat 1C | 8 HR | 7040 | 6968 | 7004 | 202 |
| rat 2A | 15 min | 6446 | 6363 | 6404.5 | 184 |
| rat 2B | 2 HR | 2699 | 2710 | 2704.5 | 75 |
| rat 2C | 8 HR | 2581 | 2563 | 2572 | 72 |
| rat 3A | 30 min | 1382 | 1413 | 1397.5 | 37 |
| rat 3B | 4 HR | 923 | 960 | 941.5 | 24 |
| rat 3C | 24 HR | 153 | 103 | 128 | 0 |
| rat 4A | 30 min | 4433 | 4328 | 4380.5 | 125 |
| rat 4B | 4 HR | 3944 | 3980 | 3962 | 112 |
| rat 4C | 24 HR | 715 | 723 | 719 | 17 |
| rat 5A | 1 HR | 13094 | 13441 | 13267.5 | 386 |
| rat 5B | 6 HR | 1028 | 1022 | 1025 | 26 |
| rat 6A | 1 HR | 3636 | 3633 | 3634.5 | 103 |
| rat 6B | 6 HR | 3243 | 3298 | 3270.5 | 92 |

TABLE 8

Rat, male, Sprague-Dowley, single oral gavage, Compound EB 100 mg/kg.

| Animal # | Blood collection time | Compound EB, Formula Weight 280 Concentration in plasma, microM |
|---|---|---|
| rat 1 | 15 min | 159 |
| rat 1 | 2 HR | 206 |

TABLE 8-continued

Rat, male, Sprague-Dowley, single oral gavage, Compound EB 100 mg/kg.

| Animal # | Blood collection time | Compound EB, Formula Weight 280 Concentration in plasma, microM |
|---|---|---|
| rat 1 | 8 HR | 202 |
| rat 2 | 15 min | 184 |
| rat 2 | 2 HR | 75 |
| rat 2 | 8 HR | 72 |
| rat 3 | 30 min | 37 |
| rat 3 | 4 HR | 24 |
| rat 3 | 24 HR | 0 |
| rat 4 | 30 min | 125 |
| rat 4 | 4 HR | 112 |
| rat 4 | 24 HR | 17 |
| rat 5 | 1 HR | 386 |
| rat 5 | 6 HR | 26 |
| rat 6 | 1 HR | 103 |
| rat 6 | 6 HR | 92 |

TABLE 9

Figure 5:
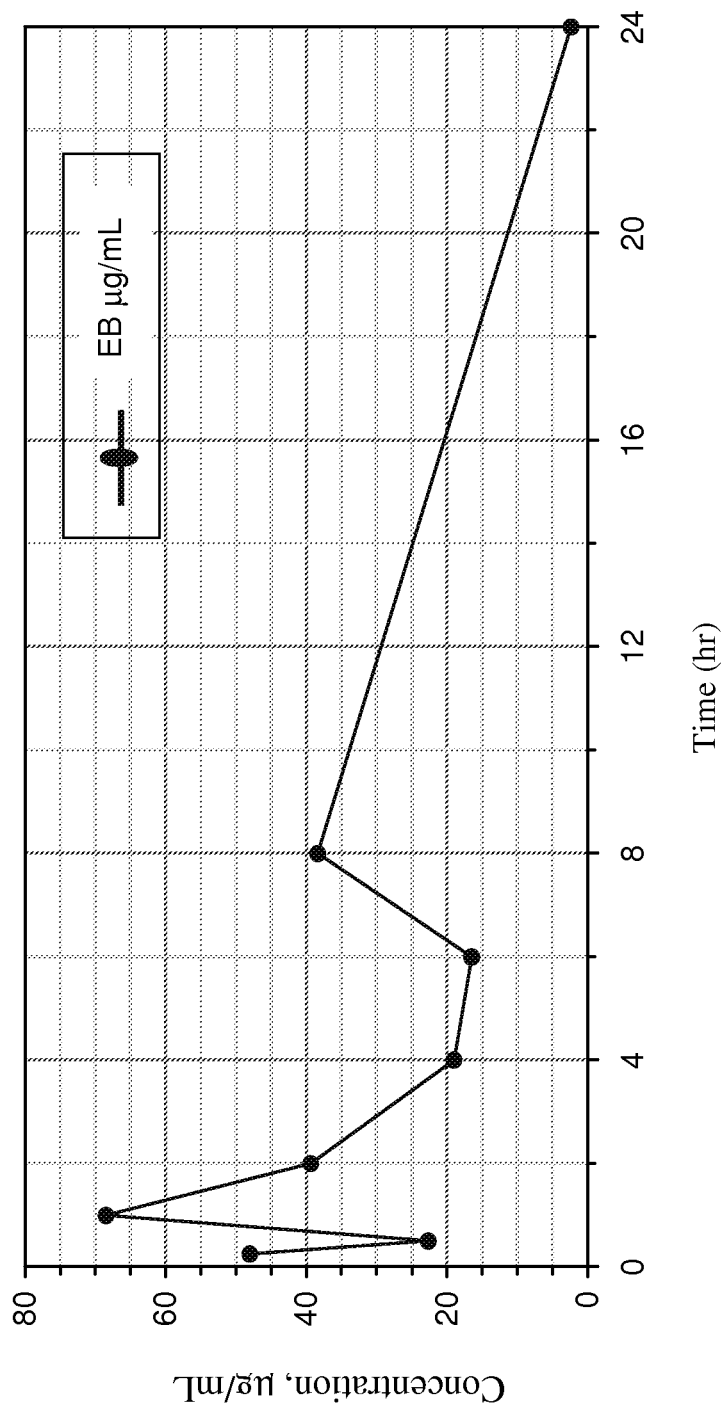
FIG. 5: Compound EB concentration in rat plasma

Compound EB concentrations, averages. (See also FIG. 5).

| Time | Compound EB µM | Compound EB µg/mL |
|---|---|---|
| 0 | 0 | 0 |
| 0.25 | 171.5 | 48.02 |
| 0.5 | 81.0 | 22.68 |
| 1 | 244.5 | 68.46 |
| 2 | 140.5 | 39.34 |
| 4 | 68.0 | 19.04 |
| 6 | 59.0 | 16.52 |
| 8 | 137.0 | 38.36 |
| 24 | 8.5 | 2.38 |

T ½ Compound EB = 3.99 hr
AUC 0-24 Compound EB = 566 µg/mL * hr
Cmax Compound EB = 108.08 µg/mL

Example 12

Rat Pilot Single-Dose Oral Pharmacokinetic Study with Compound EC

Determination of the Plasma Profile of Compound EC Following Single Oral Gavage Administration to Male Rats.

Test compound was suspended in 1% HPMC using a tissue homogenizer to minimize particles and maximize uniformity of the suspension and stored at 4° C. The formulations was thoroughly mixed just prior to administration. A dose of 100 mg/kg of test compounds or vehicle (1% HPMC) was administered to male Sprague-Dawley rats by single oral gavage. At 0, 1, 2, 4, 6, 8 and 24 hours post-dose time points, blood samples (0.4 mL) were collected by orbital sinus bleeds in $K_3$EDTA tubes. The blood samples were centrifuged within 30 minutes of collection under refrigeration (2-8° C.) for 7 minutes at 6000 rpm. Following centrifugation, the plasma were harvested into a single tube for each animal at each time point and immediately frozen at −80° C. until analyzed using LC/MS-MS. Serial plasma concentration time data was subjected to pharmacokinetic analyses using WinNonlin Standard (v2.1, Pharsight Corporation) and Microsoft EXCEL.

Protocol:

A. Plasma.

1. Rats received single oral gavage of Compound EC, 100 mg/kg, and plasma was collected at certain times.
2. Plasma was stored at −80° C. until the day of analysis.
3. Samples were thawed on 37° C. bath for 5 min and vortexed at top speed for 10 sec.
4. Rat plasma, 0.1 mL was mixed with 0.2 mL Acetonitrile, vortexed 1 min, spun down 14000 rpm, 17000 g, at 4° C., for 25 min.
5. Supernatants were filtered through 0.45 micron, 4 mm, PTFE membrane syringe filter (Phenomenex # AF0-3102-52), and 15 microL were injected and resolved on Luna 3 micron, 100A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 107 bar, 37° C. column temperature, method 406975M1, AGILENT sequence 0226-09A, Agilent 1100 LC-MS.

All samples were run in duplicate, 210 nm and 230 nm Absorbances, Negative and Positive ionization spectrograms were recorded.

B. Calibration Curve.

Step 1. Plasma from "Vehicle" animals (pooled), 0.19 mL, was mixed with 0.01 mL 20× stock of Compound EC in Methanol to make 500 microM, 250 microM, 125 microM, concentrations of Compound EC in plasma.

For example: 190 microL plasma+10 microL of 10 mM Compound EC in methanol=0.2 mL plasma with 500 microM Compound EC.

Step 2. Samples from step 1 were vortexed for 10 sec at top speed.

Step 3. 0.4 mL of acetonitrile was added to all samples from Step 2, and all vials were vortexed at top speed for 1 min.

Step 4. All samples from step 3 were spun down 14000 rpm, 17000 g, at 4° C., for 25 min.

Step 5. Supernatants were filtered through 0.45 micron, 4 mm, PTFE membrane syringe filter (Phenomenex # AF0-3102-52), 15 microL were injected and resolved on Luna 3 micron, 100A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 107 bar, 37° C. column temperature. All samples were run in duplicate, 210 nm and 230 nm Absorbances, Negative and Positive ionization spectrograms were recorded.

TABLE 10

HPLC conditions
HLPC gradient

| time min | solvent C % | solvent D % |
|---|---|---|
| 0 | 60 | 40 |
| 2 | 60 | 40 |
| 52 | 31 | 69 |
| 58 | 31 | 69 |
| 60 | 60 | 40 |
| 75 | 60 | 40 |

Figure 6:
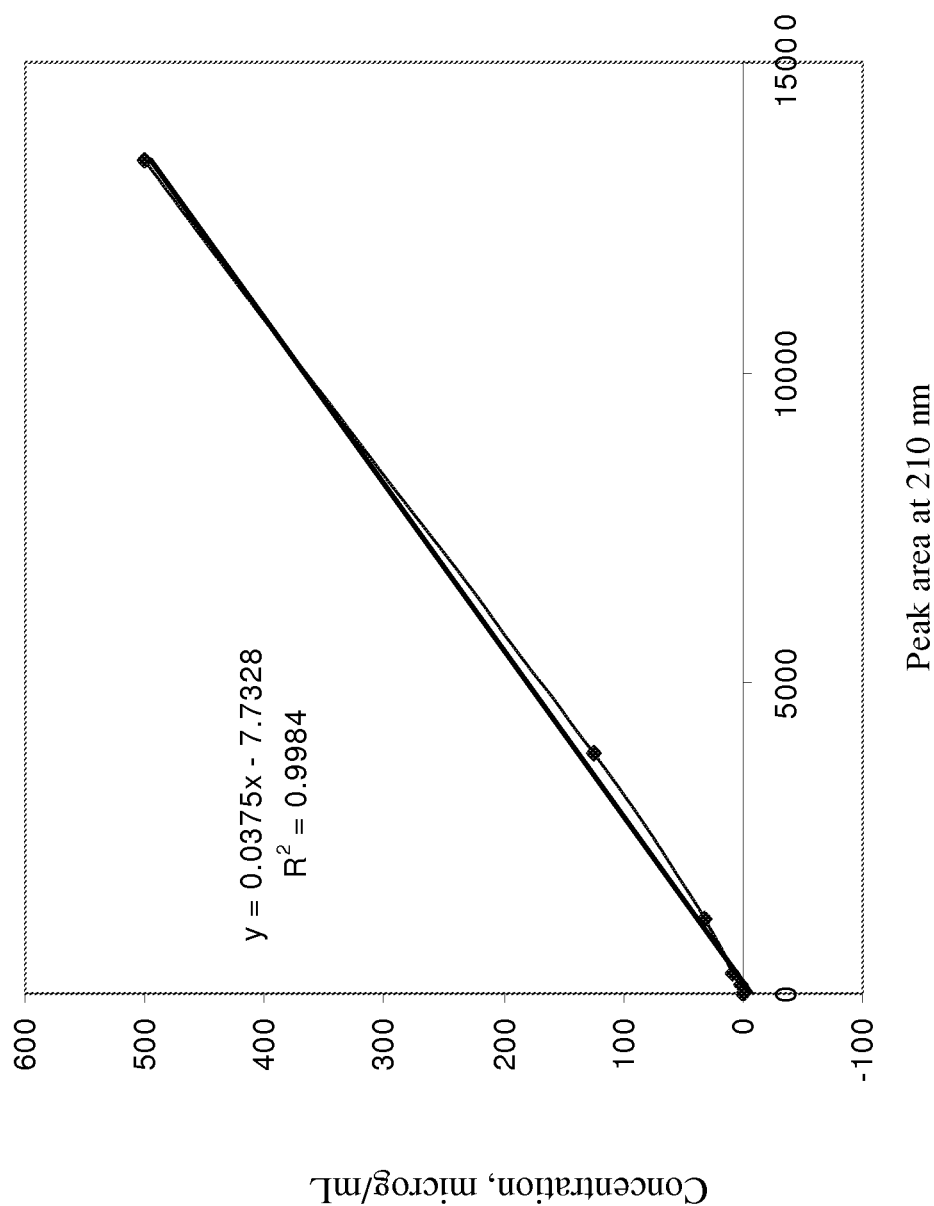
FIG. 6: Compound EC calibration curve in rat plasma, LC-MS
Figure 7:
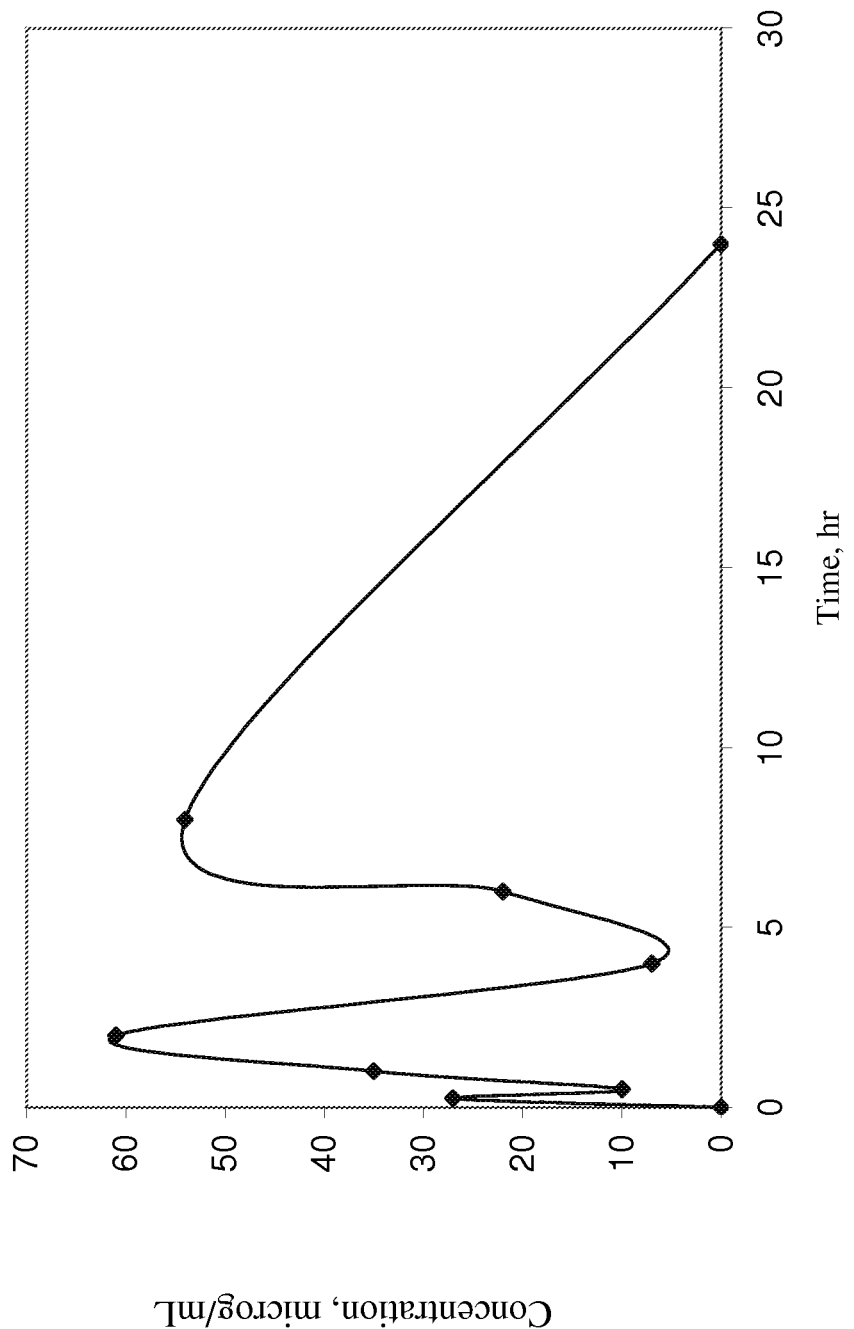
FIG. 7: Compound EC concentration in rat plasma

Solvent C: 0.1% Formic Acid in water
Solvent D: 0.1% Formic Acid, 89.9% Acetonitrile, 10% Methanol Results:

1. Calibration curve was built with RA2 fit to linearity=0.9984 (See FIG. 6).
2. Compound EC was readily detected in plasma, Retention times and mass confirmed in both Positive and Negative ionization modes. (See FIG. 7).

"M−"=293.2 100%, 527.2 65%

"M+"=295.2 100%. Formula weight 294, Retention Time average=23 min

TABLE 11

AGILENT LC-MS Sequence 0226-09A

Compound EC FW 294

| Rat plasma # | Bleed time HR | Peak area at 210 nm run 1 | run 2 | Mean | Concentration In plasma microM |
|---|---|---|---|---|---|
| 7-a | 0.25 | 2012 | 1993 | 2002.5 | 67 |
| 7-b | 2 | 979 | 963 | 971 | 29 |
| 7-c | 8 | 3059 | 3061 | 3060 | 107 |
| 8-a | 0.25 | 3263 | 3252 | 3257.5 | 114 |
| 8-b | 2 | 10470 | 10416 | 10443 | 384 |
| 8-c | 8 | 7201 | 7180 | 7190.5 | 262 |
| 9-a | 0.5 | 1401 | 1405 | 1403 | 45 |
| 9-b | 4 | 1156 | 1134 | 1145 | 35 |
| 9-c | 24 | 0 | 0 | 0 | 0 |
| 10-a | 0.5 | 864 | 862 | 863 | 25 |
| 10-b | 4 | 495 | 509 | 502 | 11 |
| 10-c | 24 | 147 | 170 | 158.5 | 0 |
| 11-a | 1 | 661 | 650 | 655.5 | 17 |
| 11-b | 6 | 2479 | 2471 | 2475 | 85 |
| 12-a | 1 | 6137 | 6119 | 6128 | 222 |
| 12-b | 6 | 2119 | 2167 | 2143 | 73 |
| 12-c | 6 | 1846 | 1865 | 1855.5 | 62 |

TABLE 12

Compound EC concentration in Rat Plasma.

| Collection Time, HR | 1st bleed | 2nd bleed | 3rd bleed | Average microM | Average microg/mL | |
|---|---|---|---|---|---|---|
| 0.25 | 67 | 114 | | 90.5 | 27 | C max |
| 0.5 | 45 | 25 | | 35 | 10 | |
| 1 | 17 | 222 | | 119.5 | 35 | |
| 2 | 29 | 384 | | 206.5 | 61 | |
| 4 | 35 | 11 | | 23 | 7 | |
| 6 | 85 | 73 | 62 | 73.33333 | 22 | |
| 8 | 107 | 262 | | 184.5 | 54 | |
| 24 | 0 | 0 | | 0 | 0 | |

TABLE 13

Compound EC concentration in Rat Plasma.

| Collection Time, HR | Average microg/mL |
|---|---|
| 0 | 0 |
| 0.25 | 27 |
| 0.5 | 10 |
| 1 | 35 |
| 2 | 61 |
| 4 | 7 |
| 6 | 22 |
| 8 | 54 |
| 24 | 0 |

Compound EC Cmax = 61 (µg/mL)
Compound EC AUC$_{0-24}$ = 672.3 (µg * hr/mL)

Example 13

Rat Pilot Single-Dose Oral Pharmacokinetic Study with Compound EG

Determination of the Plasma Profile of Compound EG Following Single Oral Gavage Administration to Male Rats.

Test compound was suspended in 1% HPMC using a tissue homogenizer to minimize particles and maximize uniformity of the suspension and stored at 4° C. The formulations was thoroughly mixed just prior to administration. A dose of 100 mg/kg of test compounds or vehicle (1% HPMC) was administered to male Sprague-Dawley rats by single oral gavage. At 0, 1, 2, 4, 6, 8 and 24 hours post-dose time points, blood samples (0.4 mL) were collected by orbital sinus bleeds in K$_3$EDTA tubes. The blood samples were centrifuged within 30 minutes of collection under refrigeration (2-8° C.) for 7 minutes at 6000 rpm. Following centrifugation, the plasma were harvested into a single tube for each animal at each time point and immediately frozen at −80° C. until analyzed using LC/MS-MS. Serial plasma concentration time data was subjected to pharmacokinetic analyses using WinNonlin Standard (v2.1, Pharsight Corporation) and Microsoft EXCEL.

Protocol:

A. Plasma.

1. Rats received single oral gavage of Compound EG, 100 mg/kg, and plasma was collected at certain times.

2. Plasma was stored at −80° C. until the day of analysis.

3. Samples were thawed on 37° C. bath for 5 min and vortexed at top speed for 10 sec.

4. Rat plasma, 0.1 mL was mixed with 0.2 mL Acetonitrile, vortexed 1 min, spun down 14000 rpm, 17000 g, at 4° C., for 25 min.

5. Supernatants were filtered through 0.45 micron, 4 mm, PTFE membrane syringe filter (Phenomenex # AF0-3102-52), and 15 microL were injected and resolved on Luna 3 micron, 100A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 107 bar, 37° C. column temperature, method 406975M1, AGILENT sequence 0226-09A, Agilent 1100 LC-MS.

All samples were run in duplicate, 210 nm and 230 nm Absorbances, Negative and Positive ionization spectrograms were recorded.

B. Calibration Curve.

Step 1. Plasma from "Vehicle" animals (pooled), 0.19 mL, was mixed with 0.01 mL 20× stock of Compound EG in Methanol to make 500 microM, 250 microM, 125 microM, . . . , concentrations of Compound EG in plasma.

For example: 190 microL plasma+10 microL of 10 mM Compound EG in methanol=0.2 mL plasma with 500 microM Compound EG.

Step 2. Samples from step 1 were vortexed for 10 sec at top speed.

Step 3. 0.4 mL of acetonitrile was added to all samples from Step 2, and all vials were vortexed at top speed for 1 min.

Step 4. All samples from step 3 were spun down 14000 rpm, 17000 g, at 4° C., for 25 min.

Step 5. Supernatants were filtered through 0.45 micron, 4 mm, PTFE membrane syringe filter (Phenomenex # AF0-3102-52), 15 microL were injected and resolved on Luna 3 micron, 100A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 107 bar, 37° C. column temperature. All samples were run in duplicate, 210 nm and 230 nm Absorbances, Negative and Positive ionization spectrograms were recorded.

TABLE 14

HPLC conditions
HLPC gradient

| time min | solvent C % | solvent D % |
|---|---|---|
| 0 | 60 | 40 |
| 2 | 60 | 40 |
| 52 | 31 | 69 |
| 58 | 31 | 69 |
| 60 | 60 | 40 |
| 75 | 60 | 40 |

Figure 8:
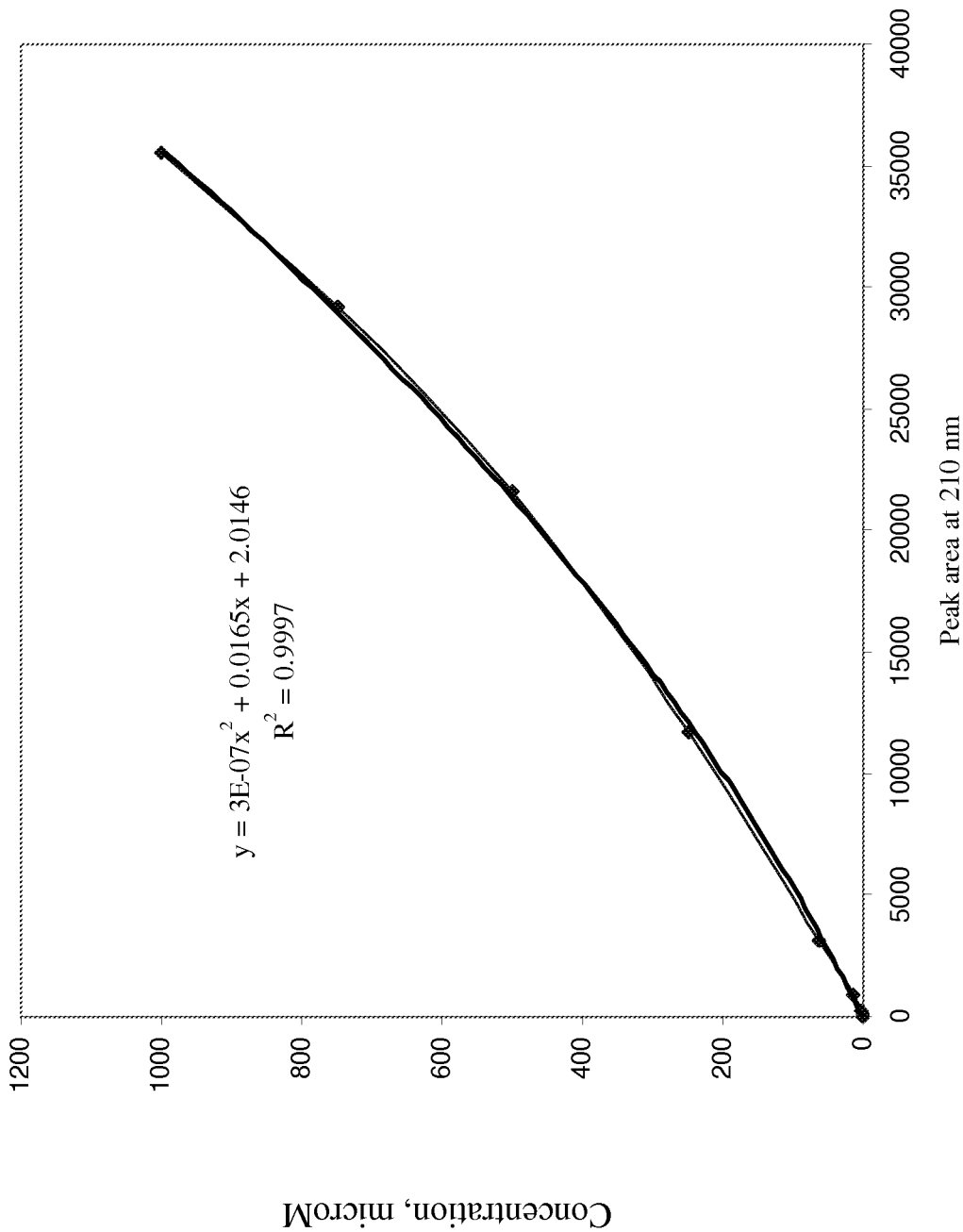
FIG. 8: Compound EG calibration curve in rat plasma, LC-MS
Figure 9:
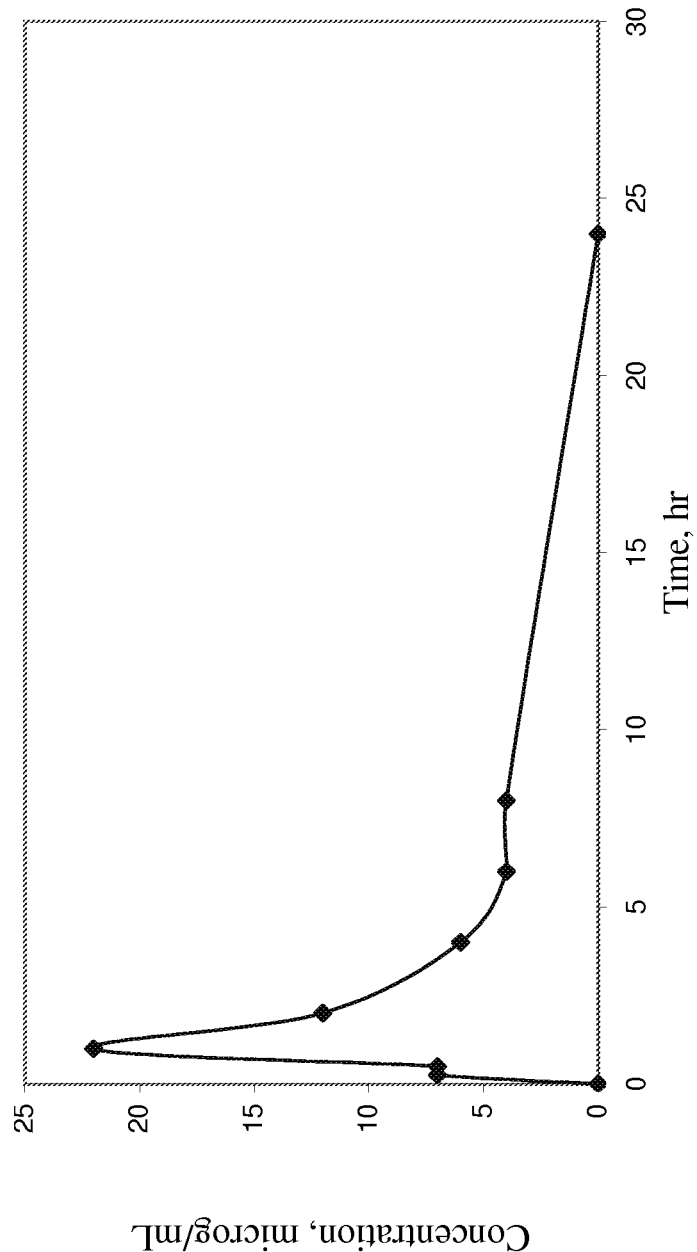
FIG. 9: Compound EG concentration in rat plasma

Solvent C: 0.1% Formic Acid in water
Solvent D: 0.1% Formic Acid, 89.9% Acetonitrile, 10% Methanol Results:

1. Calibration curve was built with RA2 fit to linearity=0.9997 (See FIG. 8).
2. Compound EG was readily detected in plasma, Retention times and mass confirmed in both Positive and Negative ionization modes. (See FIG. 9).

"M−"=307.2 100%

"M+"=309.2 100%. Formula weight 308, Retention Time average=30 min.

Raw Data and Calculations

TABLE 15

Concentration of Compound EG in rat plasma.

| | | Compound EG, Formula Weight 308 | | | |
|---|---|---|---|---|---|
| Rat plasma # | Bleed time HR | Peak area at 210 nm run 1 | run 2 | Mean | in plasma Concentr. microM |
| 13-a | 0.25 | 1484 | 1410 | 1447 | 27 |
| 13-b | 2 | 2799 | 2739 | 2769 | 50 |
| 13-c | 8 | 172 | 191 | 181.5 | 5 |
| 14-a | 0.25 | 1023 | 992 | 1007.5 | 19 |
| 14-b | 2 | 1390 | 1362 | 1376 | 25 |
| 14-c | 8 | 989 | 1029 | 1009 | 19 |
| 15-a | 0.5 | 1533 | 1596 | 1564.5 | 29 |
| 15-b | 4 | 702 | 764 | 733 | 14 |
| 15-c | 24 | 0 | 0 | 0 | 2 |
| 16-a | 0.5 | 966 | 979 | 972.5 | 18 |
| 16-b | 4 | 1234 | 1206 | 1220 | 23 |
| 16-c | 24 | 0 | 0 | 0 | 0 |
| 17-a | 1 | 5424 | 5478 | 5451 | 101 |
| 17-b | 6 | 520 | 472 | 496 | 10 |
| 18-a | 1 | 2364 | 2322 | 2343 | 42 |
| 18-b | 6 | 887 | 937 | 912 | 17 |

TABLE 16

Compound EG concentration in Rat Plasma.

| Collection Time, HR | 1st bleed | 2nd bleed | Average microM | Average microg/mL | |
|---|---|---|---|---|---|
| 0.25 | 27 | 19 | 23 | 7 | C max |
| 0.5 | 29 | 18 | 24 | 7 | |
| 1 | 101 | 42 | 72 | 22 | |
| 2 | 25 | 50 | 38 | 12 | |
| 4 | 14 | 23 | 19 | 6 | |
| 6 | 10 | 17 | 14 | 4 | |
| 8 | 5 | 19 | 12 | 4 | |
| 24 | 2 | 0 | 1 | 0 | |

TABLE 17

Compound EG concentration in Rat Plasma.

| Collection Time, HR | Average microg/mL |
|---|---|
| 0 | 0 |
| 0.25 | 7 |
| 0.5 | 7 |
| 1 | 22 |
| 2 | 12 |
| 4 | 6 |
| 6 | 4 |
| 8 | 4 |
| 24 | 0 |

Compound EG FW308 Cmax = 22 (μg/mL)
Compound EG FW 308 AUC$_{0-24}$ = 94.9 (μg * hr/mL)

What is claimed is:

1. A method for treating or preventing in a mammalian subject a condition selected from the group consisting of gout, hyperuricemia, elevated levels of uric acid that do not meet the levels customarily justifying a diagnosis of hyperuricemia, tumor-lysis syndrome, cognitive impairment associated with elevated uric acid, and *Plasmodium falciparum*-induced inflammation, comprising administering to the subject an amount of a compound represented by Formula XLVI effective to reduce the uric acid concentration in blood of, or increase uric acid excretion from, the subject

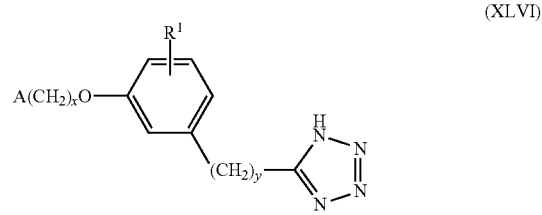

(XLVI)

wherein x is 1 or 2;

y is 0, 1, 2 or 3;

R$^1$ is selected from the group consisting of hydrogen, alkyl having 1 or 2 carbon atoms, hydroxy, alkoxy having 1 or 2 carbon atoms, fluoro, chloro, bromo, and amino; and A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy; or cycloalkyl having from 3 to 6 ring atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound by a ring carbon.

2. The method of claim 1, wherein x is 1.

3. The method of claim 1, wherein A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy.

4. The method of claim 1, wherein the compound is represented by Formula XLVII

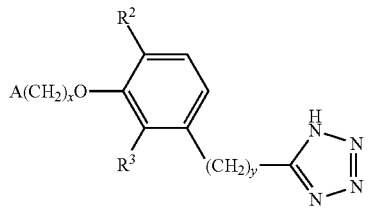

(XLVII)

wherein
x is 1 or 2;
y is 0, 1, 2 or 3;
one of $R^2$ and $R^3$ is hydrogen and the other is selected from the group consisting of hydrogen, alkyl having 1 or 2 carbon atoms, hydroxy, alkoxy having 1 or 2 carbon atoms, fluoro, chloro, bromo, and amino; and
A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy; or
cycloalkyl having from 3 to 6 ring atoms wherein the cycloalkyl is unsubstituted or one or two ring carbons are independently mono-substituted by methyl or ethyl; or
a 5 or 6 membered heteraromatic ring having 1 or 2 ring heteroatoms selected from N, S and O and the heteroaromatic ring is covalently bound to the remainder of the compound by a ring carbon.

5. The method of claim 4, wherein x is 1.

6. The method of claim 4, wherein A is phenyl, unsubstituted or substituted by one, two or three groups selected from the group consisting of halo, alkyl having 1 or 2 carbon atoms, perfluoromethyl, alkoxy having 1 or 2 carbon atoms, and perfluoromethoxy.

7. The method of claim 6, wherein A is 2,6-dimethylphenyl or 2,6-difluorophenyl.

8. The method of claim 6, wherein the compound is represented by Formula XLVIII

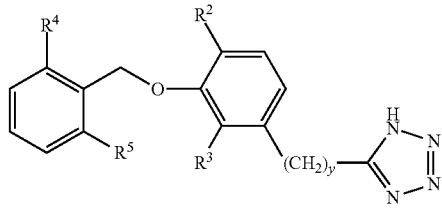

(XLVIII)

wherein
y is 0, 1 or 2;
one of $R^2$ and $R^3$ is hydrogen and the other is selected from the group consisting of hydrogen, alkyl having 1 or 2 carbon atoms, hydroxy, alkoxy having 1 or 2 carbon atoms, fluoro, chloro, bromo, and amino; and
$R^4$ and $R^5$ are independently selected from the group consisting of methyl, fluoro and chloro.

9. The method of claim 1, wherein the condition is selected from the group consisting of gout and hyperuricemia.

10. The method of claim 1, wherein the subject is a human.

11. The method of claim 1, further comprising administering to the subject one or more other uric acid lowering drugs in a combined amount effective to reduce the uric acid concentration in blood of, or increase uric acid excretion from, the subject.

12. The method of claim 11, wherein the other uric acid lowering drug is selected from the group consisting of a xanthine oxidase inhibitor, a uricosuric agent, a urate transporter-1 inhibitor, a uricase, and a statin.

13. The method of claim 11, wherein the other uric acid lowering drug is administered in an amount that is less than the usual therapeutic dose when administered alone.

14. The method of claim 11, wherein the compound and the one or more other uric acid lowering drugs are mixed together to form an admixture and the admixture is administered to the subject.

15. The method of claim 11, wherein the compound and the one or more other uric acid lowering drugs are not mixed together to form an admixture but are administered independently to the subject.

16. The method of claim 1, wherein the compound is formulated for oral administration.

* * * * *